United States Patent
Wang et al.

(10) Patent No.: US 10,535,824 B2
(45) Date of Patent: Jan. 14, 2020

(54) ORGANIC ELECTROLUMINESCENT MATERIAL AND ORGANIC OPTOELECTRONIC DEVICE

(71) Applicants: Shanghai Tianma AM-OLED Co., Ltd., Shanghai (CN); Tianma Micro-Electronics Co., Ltd., Shenzhen (CN)

(72) Inventors: Xiangcheng Wang, Shanghai (CN); Ying Liu, Shanghai (CN); Hongyang Ren, Shanghai (CN); Wei He, Shanghai (CN); Chen Liu, Shanghai (CN)

(73) Assignees: SHANGHAI TIANMA AM-OLED CO., LTD., Shanghai (CN); TIANMA MICRO-ELECTRONICS CO., LTD., Shenzhen (CN)

( * ) Notice: Subject to any disclaimer, the term of this patent is extended or adjusted under 35 U.S.C. 154(b) by 302 days.

(21) Appl. No.: 15/599,009

(22) Filed: May 18, 2017

(65) Prior Publication Data
US 2017/0256718 A1   Sep. 7, 2017

(30) Foreign Application Priority Data
Dec. 30, 2016  (CN) .......................... 2016 1 1264701

(51) Int. Cl.
*H01L 51/00* (2006.01)
*C09K 11/06* (2006.01)
(Continued)

(52) U.S. Cl.
CPC ........ *H01L 51/0053* (2013.01); *C07D 413/04* (2013.01); *C07D 413/10* (2013.01);
(Continued)

(58) Field of Classification Search
CPC .. C07D 413/04; C07D 413/10; C07D 413/14; C07D 417/14; C09K 11/02; C09K 11/06;
(Continued)

(56) References Cited

U.S. PATENT DOCUMENTS

2017/0288149 A1* 10/2017 Danz ................... H01L 51/0053

FOREIGN PATENT DOCUMENTS

| CN | 104011894 A | 8/2014 |
| TW | 201627284 A | 8/2016 |
| WO | 2016116504 A1 | 7/2016 |

OTHER PUBLICATIONS

Machine translation for WO 2016/116504 (publication date: Jul. 2016). (Year: 2016).*

* cited by examiner

*Primary Examiner* — Dawn L Garrett
(74) *Attorney, Agent, or Firm* — Anova Law Group PLLC

(57) ABSTRACT

A compound and an organic optoelectronic device are provided. The compound has the chemical formula (I):

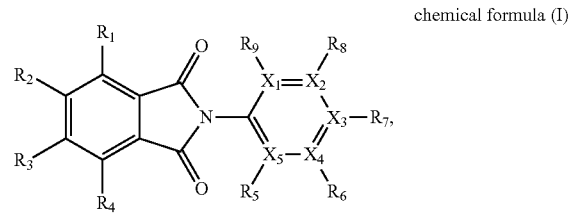

chemical formula (I)

wherein: $X_1$ to $X_5$ are independently selected from C and N, when N is selected, a substituent may not be included; $R_1$ to
(Continued)

$R_9$ are independently selected nom hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II):

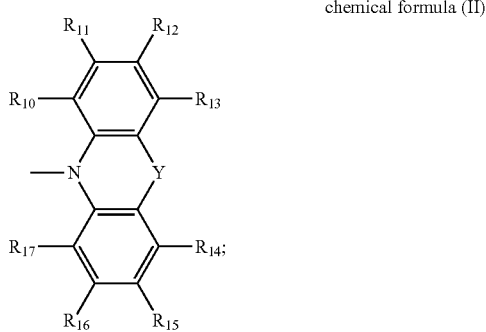

chemical formula (II)

and at least one of $R_1$ to $R_9$ is selected from the chemical group A. In the chemical formula (II), $R_{10}$ to $R_{17}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, and Y is selected from O, S, substituted or unsubstituted imino, substituted or unsubstituted methylene, and substituted or unsubstituted silylene.

19 Claims, 4 Drawing Sheets

(51) Int. Cl.
  *C09K 11/02* (2006.01)
  *C07D 413/10* (2006.01)
  *C07D 413/14* (2006.01)
  *C07D 413/04* (2006.01)
  *H01L 51/50* (2006.01)
  *C07D 417/14* (2006.01)
  *H05B 33/14* (2006.01)
(52) U.S. Cl.
  CPC ......... *C07D 413/14* (2013.01); *C07D 417/14* (2013.01); *C09K 11/02* (2013.01); *C09K 11/06* (2013.01); *H01L 51/0071* (2013.01); *H05B 33/14* (2013.01); *C09K 2211/1007* (2013.01); *C09K 2211/1018* (2013.01); *H01L 51/0067* (2013.01); *H01L 51/5016* (2013.01)
(58) Field of Classification Search
  CPC .... C09K 2211/1007; C09K 2211/1018; H01L 51/0053; H01L 51/0067; H01L 51/0071; H01L 51/5016; H05B 33/14
  See application file for complete search history.

ORGANIC ELECTROLUMINESCENT MATERIAL AND ORGANIC OPTOELECTRONIC DEVICE

CROSS-REFERENCES TO RELATED APPLICATIONS

This application claims priority of Chinese Patent Application No. 201611264701.1, filed on Dec. 30, 2016, the entire contents of which are hereby incorporated by reference.

FIELD OF THE DISCLOSURE

The present disclosure generally relates to the field of organic electroluminescent material, and, more particularly, relates to an organic electroluminescent material and an organic optoelectronic device thereof.

BACKGROUND

Recently, organic light-emitting diodes (OLEDs) are emerging as a new generation of display products, because of various advantages such as self-luminous, high efficiency, wide color gamut, and wide viewing angle. Organic electroluminescent materials play a critical role for the continuous development of OLEDs.

The organic electroluminescent materials can be excited to generate singlet excited state ($S_1$) excitons and triplet excited state ($T_1$) excitons. According to the spin statistics, the ratio of the $S_1$ excitons to the $T_1$ excitons is 1:3. According to different light-emitting mechanisms, the existing organic electroluminescent materials are often categorized into fluorescent materials, phosphorescent materials, triplet-triplet annihilation (TTA) materials, and heat activated delayed fluorescence (TADF) materials.

TADF materials have the advantages of high quantum yield and low production cost, and comparable luminous efficiency as the phosphorescent material. TADF materials are expected to be new organic electroluminescent materials with great applications. However, the choices of the existing TADF materials are rather limited, and the performance of the TADF materials has not been improved yet. Diverse and high performance TADF materials are highly desired.

The disclosed organic electroluminescent material and organic optoelectronic device thereof are directed to solve one or, more problems set forth above and other problems.

BRIEF SUMMARY OF THE DISCLOSURE

One aspect of the present disclosure provides a compound of the following chemical formula (I):

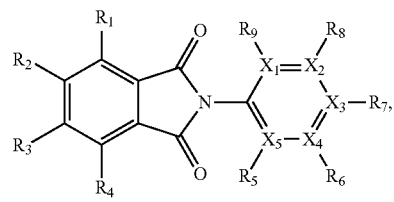

chemical formula (I)

wherein:

in the chemical formula (I), $X_1$ to $X_5$ are independently selected from C and N, when N is selected, a substituent may not be included; $R_1$ to $R_9$ are independently selected from hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II); and at least one of $R_1$ to $R_9$ is selected from the chemical group A,

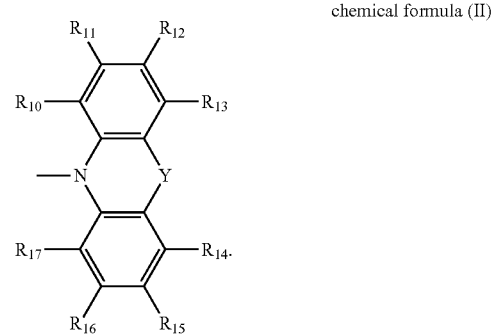

chemical formula (II)

In the chemical formula (II), $R_{10}$ to $R_{17}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, and Y is selected from O, S, substituted or unsubstituted imino, substituted or unsubstituted methylene, and substituted or unsubstituted silylene, and a substituent is selected from hydrogen, deuterium, $C_1$ to $C_{30}$ alkyl, $C_1$ to $C_{30}$ heteroatom-substituted $C_6$ to $C_{30}$ aryl, and $C_2$ to $C_{30}$ heteroaryl.

Another aspect of the present disclosure provides an organic optoelectronic device, The organic optoelectronic device comprises an anode; a cathode; and one or more organic thin film layers disposed between the anode and the cathode. At least one of the one or more organic thin film layers includes one or more organic electroluminescent compounds each having the following chemical formula (I):

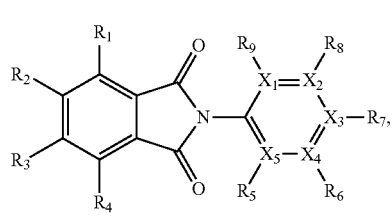

chemical formula (I)

wherein:

in the chemical formula (I), $X_1$ to $X_5$ are independently selected from C and N, when N is selected, a substituent may not be included; $R_1$ to $R_9$ are independently selected from hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II); and at least one of $R_1$ to $R_9$ is selected from the chemical group A,

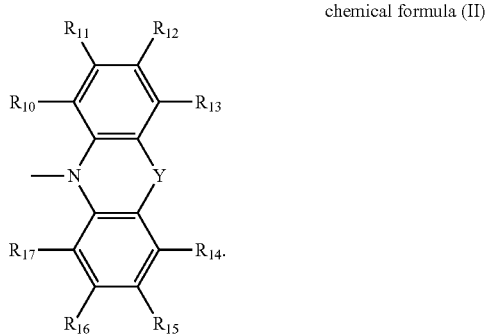

chemical formula (II)

In the chemical formula (II), $R_{10}$ to $R_{17}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, and Y is selected from O, S, substituted or unsubstituted imino, substituted or unsubstituted methylene, and substituted or unsubstituted silylene, and a substituent is selected from hydrogen, deuterium, $C_1$ to $C_{30}$ alkyl $C_1$ to $C_{30}$ heteroatom-substituted alkyl, $C_6$ to $C_{30}$ aryl, and $C_2$ to $C_{30}$ heteroaryl.

Other aspects of the present disclosure can be understood by those skilled in the art in light of the description, the claims, and the drawings of the present disclosure.

DESCRIPTION OF THE DRAWINGS

The following drawings are merely examples for illustrative purposes according to various disclosed embodiments and are not intended to limit the scope of the present disclosure.

In FIGS. 1-5 and 7, the various reference numerals and corresponding names are as follows: 100—substrate; 110—anode; 120—cathode; 130—light—emitting layer; 140—hole transport layer (HTL); 150—electron transport layer (ETL); 160—hole injection layer (HIL); 170—electron injection layer (EIL); 180—electron blocking layer (EBL); and 190—hole blocking layer (HBL).

DETAILED DESCRIPTION

Figure 1:
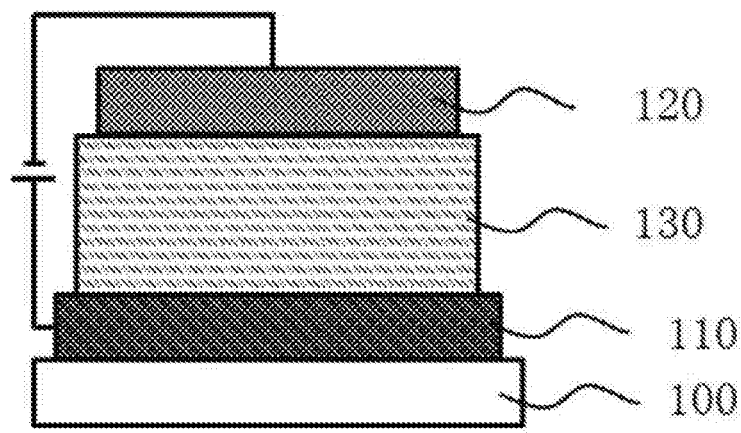
FIG. 1 illustrates a schematic diagram of an exemplary organic light-emitting diode (OLED) consistent with disclosed embodiments.

Reference will now be made in detail to exemplary embodiments of the disclosure, which are illustrated in the accompanying drawings. Hereinafter, embodiments consistent with the disclosure will be described with reference to drawings. In the drawings, the shape and size may be exaggerated, distorted, or simplified for clarity. Wherever possible, the same reference numbers will be used throughout the drawings to refer to the same or like parts, and a detailed description thereof may be omitted.

Further, in the present disclosure, the disclosed embodiments and the features of the disclosed embodiments may be combined under conditions without conflicts. It is apparent that the described embodiments are some but not all of the embodiments of the present disclosure. Based on the disclosed embodiments, persons of ordinary skill in the art may derive other embodiments consistent with the present disclosure, all of which are within the scope of the present disclosure.

As discussed in the background, according to different light-emitting mechanisms, the existing organic electroluminescent materials are often categorized into fluorescent materials, phosphorescent materials, triplet-triplet annihilation (TTA) materials, and heat activated delayed to fluorescence (TADF) materials. In fluorescent materials, S1 excitons transit to the ground state $S_0$ by radiation, thereby emitting light. The material cost is substantially low, however, due to the limited number of $S_1$ excitons (i.e., accounting for 25% of the excitons generated by the organic electroluminescent material), the quantum efficiency is substantially low.

Phosphorescent materials not only utilize $S_1$ excitons accounting for 25% of the excitons generated by the organic electroluminescent material, but also utilize $T_1$ excitons accounting for 75% of the excitons generated by the organic electroluminescent material. Thus, the theoretical quantum efficiency of phosphorescent materials is up to 100%, and when used as organic electroluminescent materials for the OLEDs, the phosphorescent materials has significantly improved the luminous efficiency as compared to the fluorescent materials. However, the phosphorescence materials are limited to Ir, Pt, Os, Re, Ru and other heavy metal complexes. The production cost is higher, and the structure is substantially simple.

TTA materials utilize two $T_1$ excitons interactions to produce one $S_1$ exciton that transitions hack to the ground state $S_0$ by radiation. Although $T_1$ excitons are utilized, the production cost is not high, and the theoretical maximum quantum yield of TTA, materials is only about 62.5%. The practical applications of TTA materials are still rather limited, TADF materials utilize both $S_1$ excitons accounting for 25% of the excitons generated by the organic electroluminescent material, and $T_1$ excitons accounting for 75% of the excitons generated by the organic electroluminescent material. Thus, the theoretical quantum efficiency of TTA materials is up to 100%. TADF materials are mainly aromatic organic materials without rare metal elements, and the production cost is substantially low.

According to the above discussion of various existing organic electroluminescent materials, TADF materials have high quantum yield, low production cost, and comparable luminous efficiency as the phosphorescent material. TADF materials are expected to be organic electroluminescent materials with great application prospect. However, the choices of the existing TADF materials are rather limited, and the performance the TADF materials has to be improved. Diverse and high performance TADF materials are highly desired.

The present disclosure provides an organic electroluminescent material to be used in an organic optoelectronic device, and an organic optoelectronic device thereof.

Unless otherwise defined, all technical, and scientific terms used herein have the same meaning as commonly understood by one of ordinary skill in the art to which this disclosure belongs. In case of conflict, the present specification, including definitions, will control. In addition, the materials, methods, and examples are for illustrative only and not intended to limit the scope of the present disclosure.

When no other definition is provided, the term "substituted" used herein means that the hydrogen of the compound is substituted with at least one of the following groups: halogen (F, Cl, Br or I), hydroxy, alkoxy, nitro, cyano, amino, azido, amidino, nitrite, carbonyl, carbamoyl, thiol, ester, carboxyl or salt thereof, sulfonic acid group or salt thereof, phosphoric acid group or salt thereof, $C_1$ to $C_{30}$ alkyl group, $C_2$ to $C_{20}$ alkenyl group, $C_2$ to $C_{20}$ alkynyl group, $C_6$ to $C_{30}$ aryl group, $C_7$ to $C_{20}$ aralkyl group, $C_1$ to $C_8$ alkoxy group, $C_3$ to $C_{20}$ heteroaryl group, and $C_3$ to $C_{30}$ cycloalkyl.

Alkyl group refers to a hydrocarbyl group that is fully saturated (without double or triple bond), which may be linear or branched, or cycloalkyl, and may also be a straight or branched chain containing a cycloalkyl substituent chain. The alkyl group may contain 1 to 30 carbon atoms, 1 to 20 carbon atoms, 1 to 10 carbon atoms or 1 to 6 carbon atoms. The numerical range of "1 to 30" refers to all integers in the range, including 1, 2, 3, 4, 5, 6, 7, 8, 9, 10, 11, 12, 13, 14, 15, 16, 17, 20, 21, 22, 23, 24, 25, 26, 27, 28, 29 or 30. The alkyl group may include, but not limited to, methyl, ethyl, propyl, isopropyl, n-butyl, isobutyl, sec-butyl, tert-butyl, pentyl and hexyl. The alkyl group may be substituted or unsubstituted.

Heteroatom-substituted alkyl group includes an alkyl group substituted at any position by a heteroatom. For example, the heteroatom-substituted alkyl group may be attached to the compound nucleus by a heteroatom, i.e., in a "—Z-alkyl" form, where Z may represent a heteroatom such as O (i.e., oxygen atom), S (i.e., sulfur atom). The heteroatom-substituted alkyl group may also be an alkoxy group. The heteroatom-substituted alkyl group may include 1 to 30 carbon atoms, 1 to 20 carbon atoms, 1 to 10 carbon atoms or 1 to 6 carbon atoms. The numerical range of "1 to 30" refers to all integers in the range, including 1, 2, 4, 5, 6, 7, 8, 9, 10, 11, 12, 13, 14, 15, 16, 17, 20, 21, 22, 23, 24, 25, 26, 27, 28, 29 or 30. The alkoxy group may include, but not limited to, methoxy, ethoxy, propoxy, isopropoxy, and butoxy. The heteroatom-substituted alkyl group may be substituted or unsubstituted.

Aromatic or Aryl group refers to carbocyclic (all carbon) having a completely delocalized π-electron system over all rings, including monocyclic aromatic or polycyclic aromatic groups. The polycyclic aromatic group may include two or more aromatic rings, such as a benzene ring, which are linked to each other by a single bond or by mutual chemical bonds. The number of carbon atoms in the aryl group may vary. For example, the aryl group may contain 6 to 30 carbon atoms. For example, a numerical range of 6 to 30 refers to all integers in the range, including 6, 7, 8, 9, 10, 11, 12, 13, 14, 15, 16, 17, 18, 19, 20, 21, 22, 23, 24, 25, 76, 27, 28, 29 or 30. The aryl group may include, but be not limited to, benzene, biphenyl, naphthalene, anthracene, phenanthrene or pyrene. The aryl group may be substituted or unsubstituted.

Heteroaryl group refers to a monocyclic or polycyclic aromatic ring system comprising one or more heteroatoms in which the heteroatoms are elements other than carbon, including but not limited to nitrogen, oxygen and sulfur. The number of carbon atoms in the heteroaryl ring may vary. For example, the heteroaryl group may include 1 to 20 carbon atoms in the ring, and a numerical range of 1-20 refers to all integers in the range, including 1, 2, 3, 4, 7, 8, 9, 10, 11, 12, 13, 14, 15, 16, 17, 18, 19 or 20. For example, the heteroaryl group may include 1 to 30 ring skeleton atoms in its ring, for example, a numerical range of 1-30 refers to all integers in the range, including 1, 2, 3, 11, 12, 13, 14, 15, 16, 17, 18, 19, 20, 71, 22, 23, 24, 25, 26, 27, 28, 29 or 30.

In addition, the heteroaryl group may include a fused ring system in which two rings, such as at least one aryl ring and at least one heteroaryl ring or at least two hetero aryl rings, share at least one chemical bond. For example, the heteroaryl ring may include, but not limited to, furan, furazan, thiophene, benzothiophene, phthalazine, pyrrole, oxazole, benzoxazole, 1,2,3-oxadiazole, oxadiazole, thiazole, 1,2,3-thiadiazole 1,2,4-thiadiazole, benzothiazole, imidazole, benzimidazole, indole, indazole, pyrazole, benzopyrazole, Isoxazole, benzisoxazole, isothiazole, triazole, benzotriazole, thiadiazole, tetrazole, pyridine, pyridazine, pyrimdine, pyrazine, purine, pteridine, quinoline, isoquinoline, auinazoline, quinoxaline, cinnoline and triazine. The heteroaryl group may be substituted or unsubstituted.

The present disclosure provides an organic electroluminescent material comprising a compound of the following chemical formula (I):

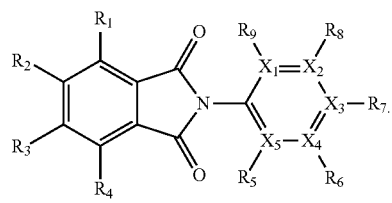

chemical formula (I)

In the chemical formula (I), $X_1$ to $X_5$ may be independently selected from C and N, when N is selected, a substituent may not, be included. $R_1$ to $R_9$ may be independently selected from hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II):

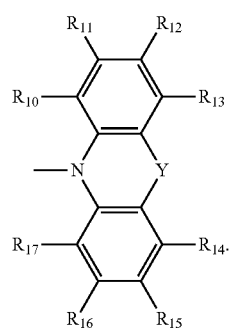

chemical formula (II)

At least one of $R_1$ to $R_9$ may be selected from the chemical group A.

In the chemical formula (II), $R_{10}$ to $R_{17}$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Y may be selected from O, S, substituted or unsubstituted imino, substituted or unsubstituted methylene, and substituted or unsubstituted silylene, and a substituent may be selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl.

In certain embodiments, the disclosed compounds may have also the following chemical formula (III):

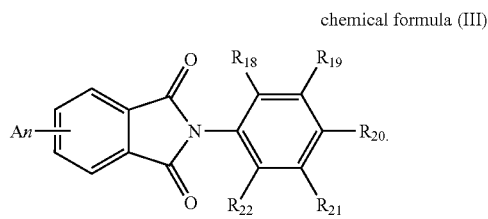

chemical formula (III)

In the chemical formula (III), $R_{18}$ to $R_{22}$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. n is a positive integer and $1 \le n \le 4$.

In certain other embodiments, the disclosed compounds may have also the following chemical formula (IV):

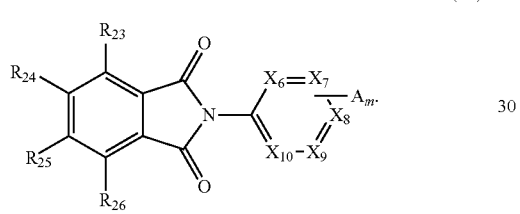

chemical formula (IV)

In the chemical formula (IV), $X_6$ to $X_{10}$ may be independently selected from C and N, and at least three of $X_6$ to $X_{10}$ may be selected from C. When N is selected, a substituent may not be included, while when C is selected, a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl may be included, $R_{23}$ to $R_{26}$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. m is a positive integer and $1 \le m \le 5$. The chemical group A may be connected C of $X_6$ to $X_{10}$.

In one embodiment, the heteroatom-substituted alkyl may be selected from alkoxy groups.

In one embodiment, the $C_6$ to $C_{30}$ aryl may be selected from phenyl and naphthyl.

In one embodiment, the $C_2$ to $C_{30}$ heteroaryl may be selected from heteroaryl containing one or more N.

In one embodiment, the chemical group A may be selected from the following groups:

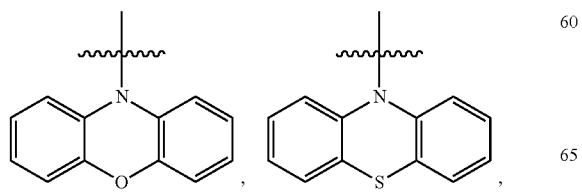

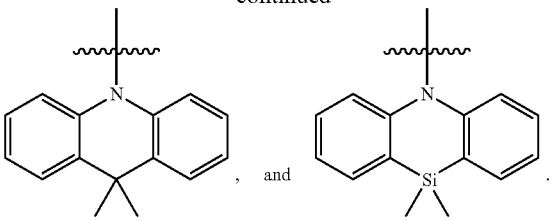

Certain examples of the disclosed compounds are shown below as Compounds 1-83, which are for illustrative purposes and are not intended to limit the scope of the present discourse.

1

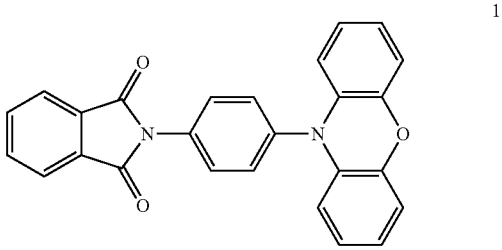

2

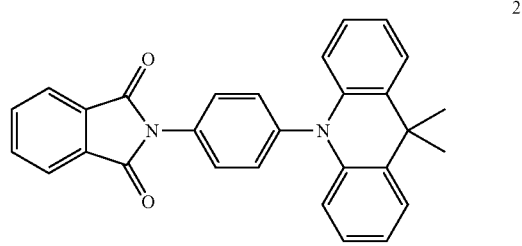

3

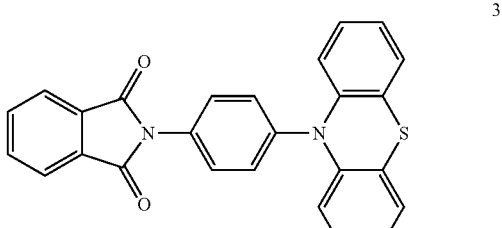

4

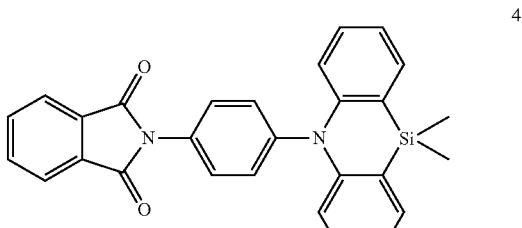

5

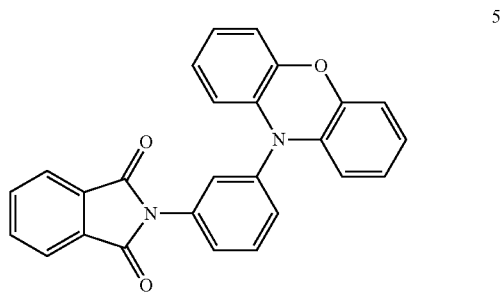

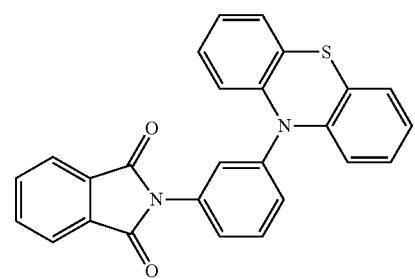
6
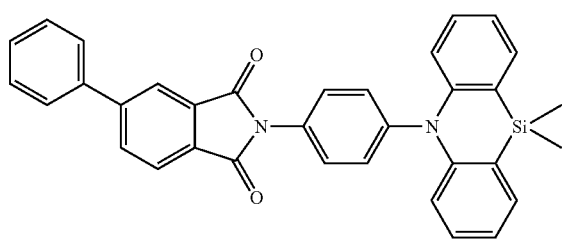
12
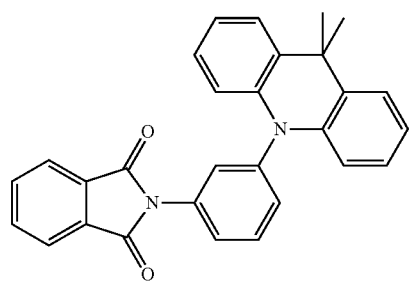
7
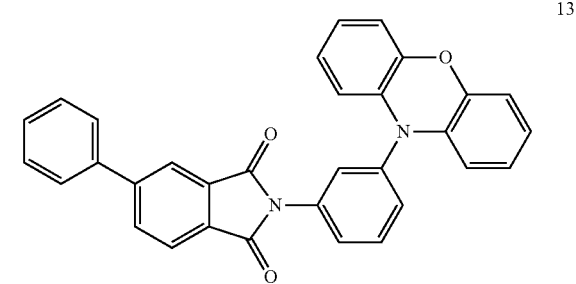
13
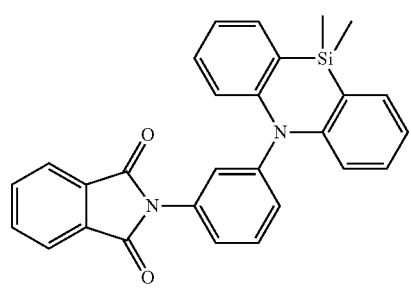
8
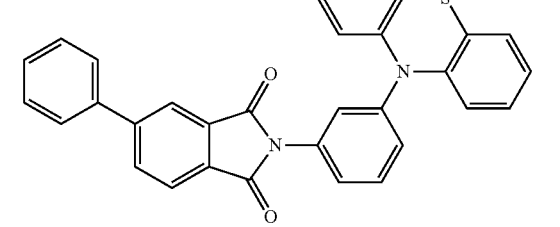
14
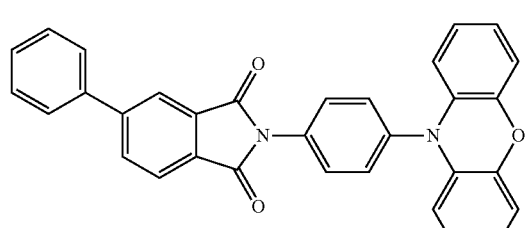
9
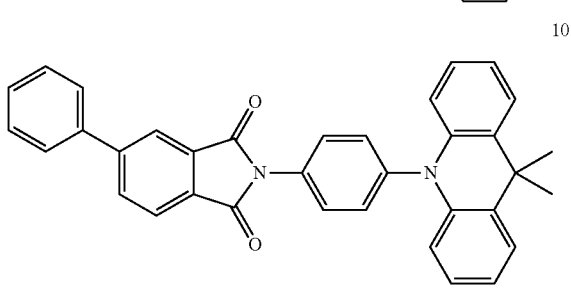
10
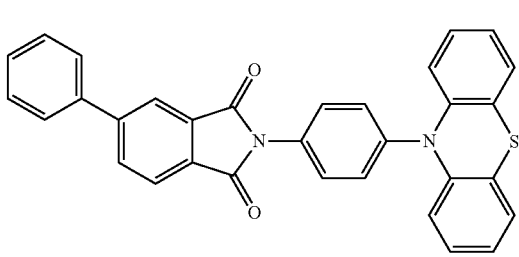
11
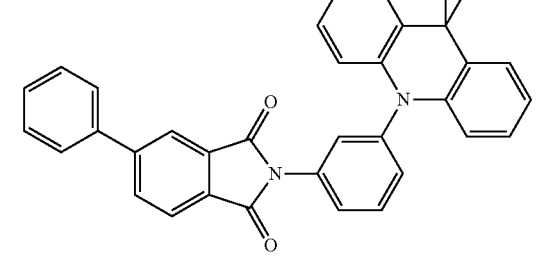
15
16

17 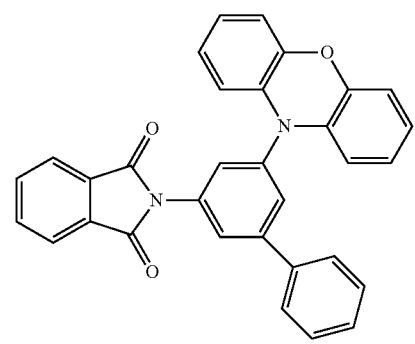
18 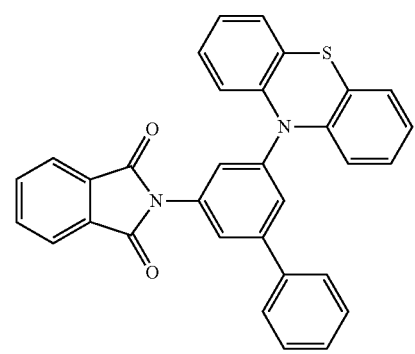
19 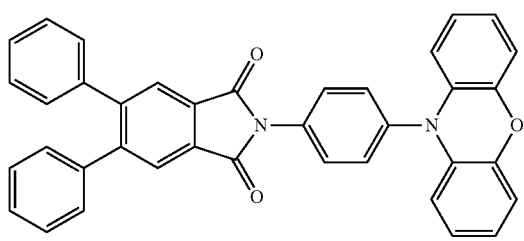
20 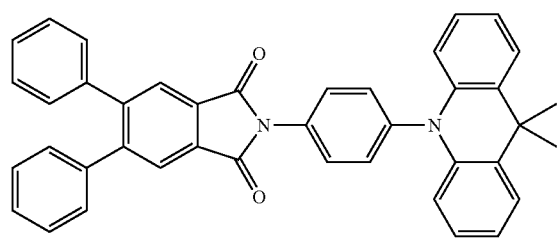
21 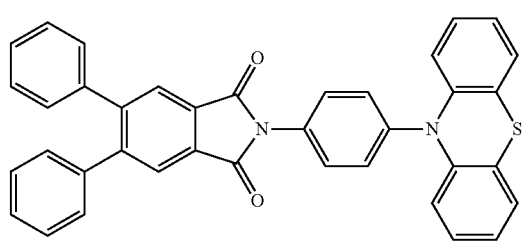
22 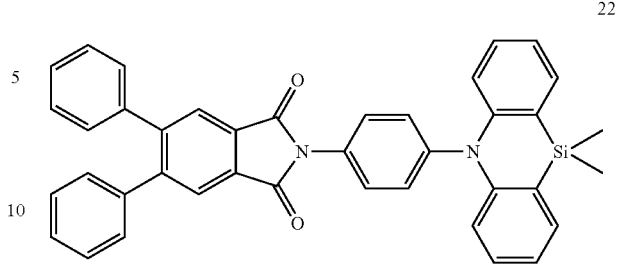
23 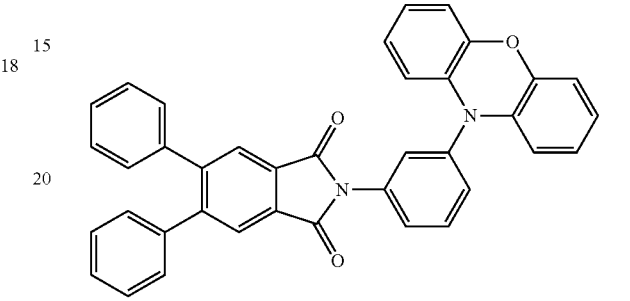
24 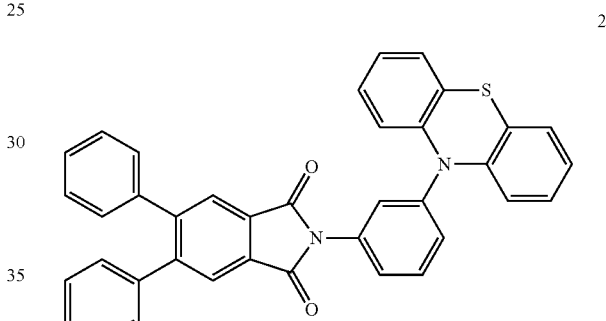
25 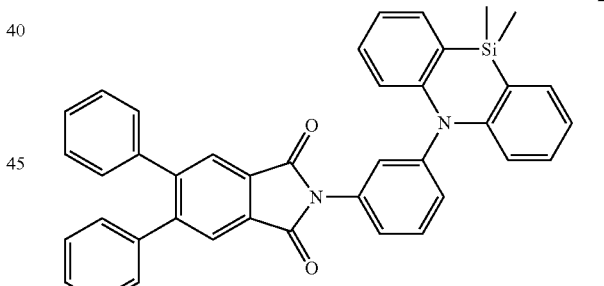
26 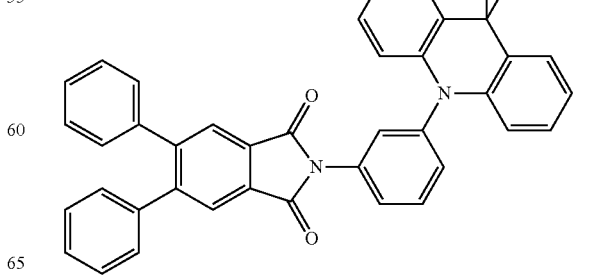

27
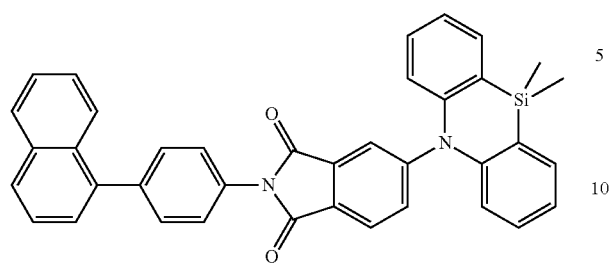
28
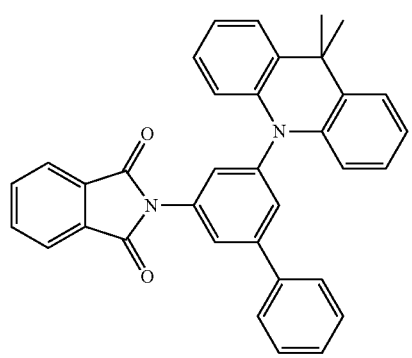
29
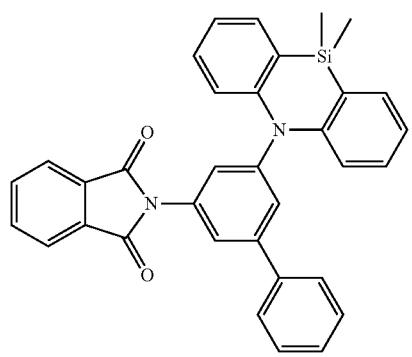
30
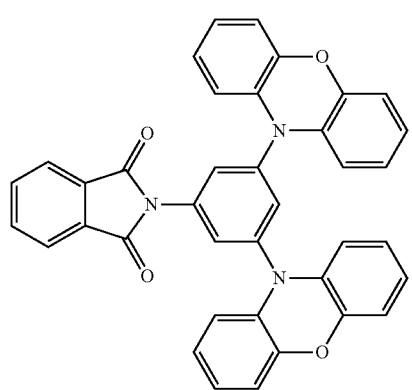
31
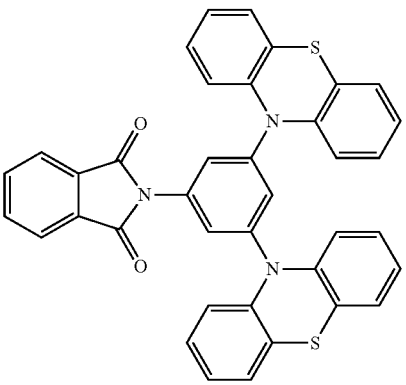
32
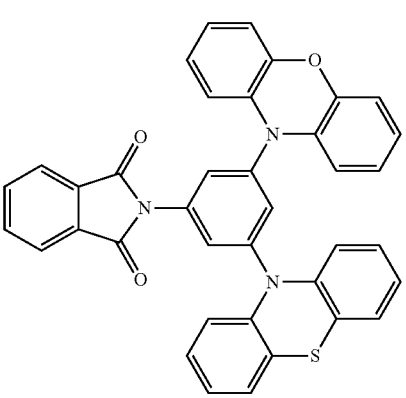
33
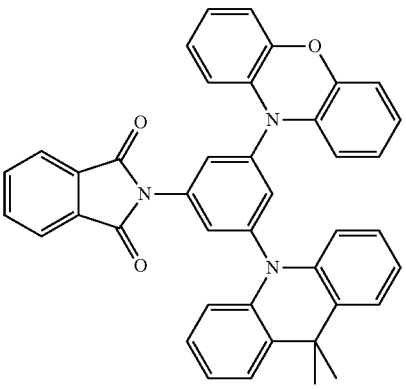
34
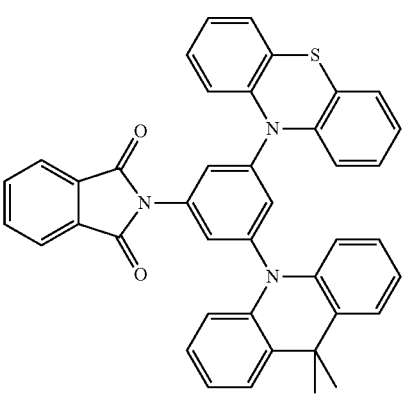

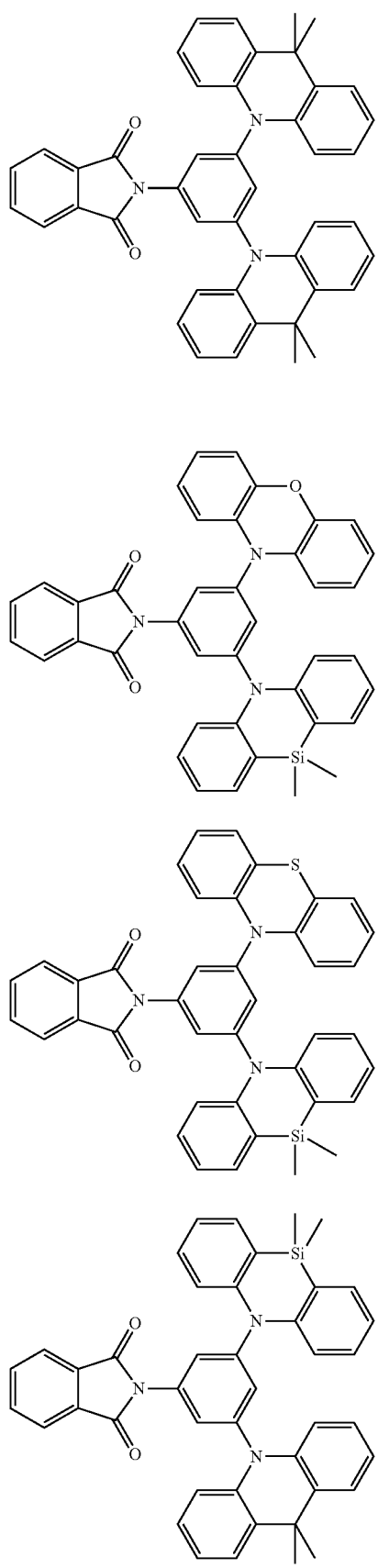
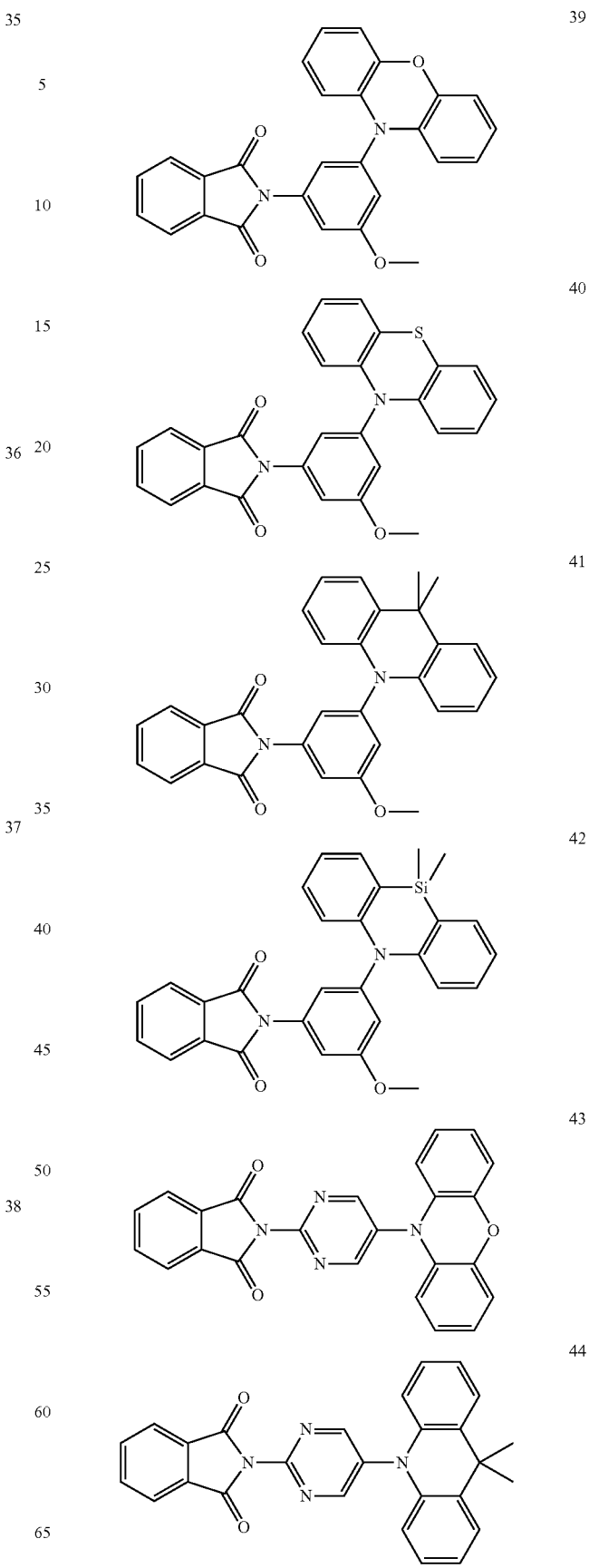

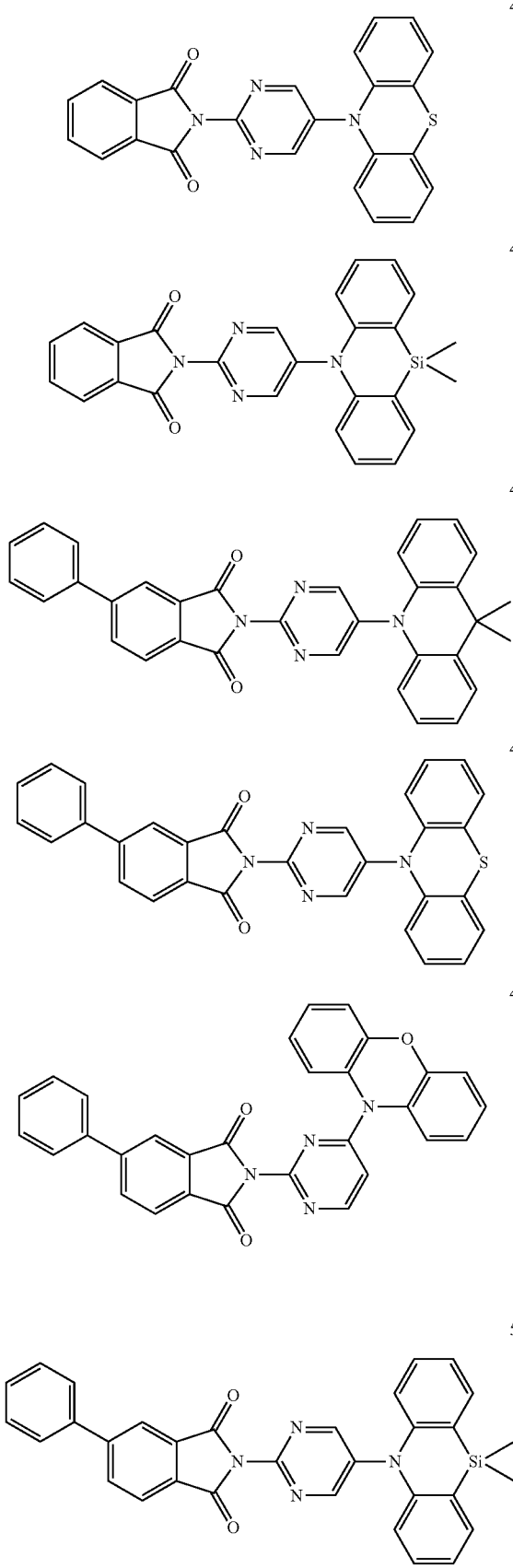

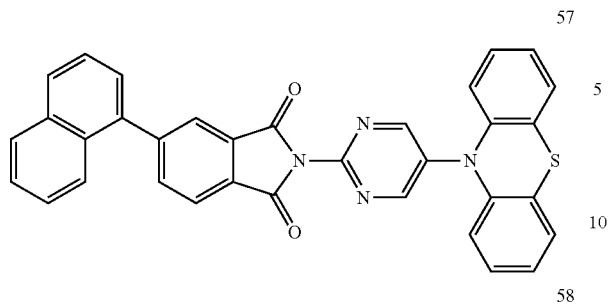
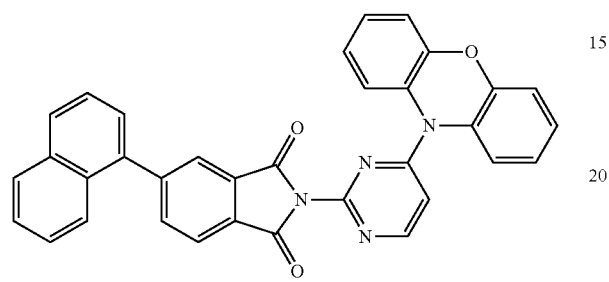
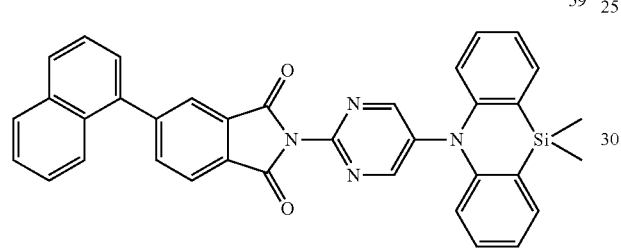
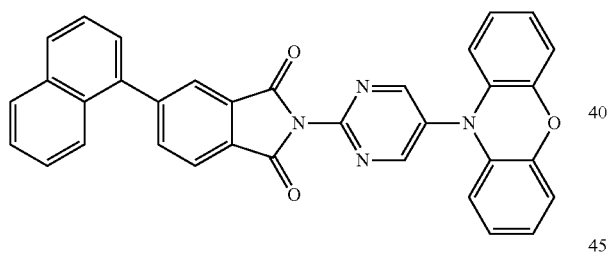
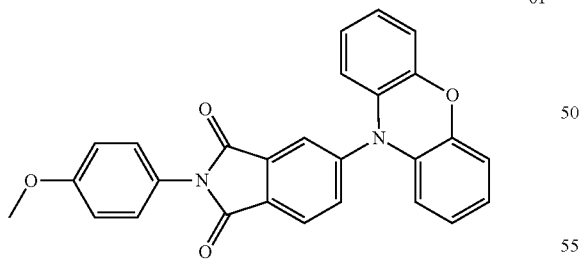
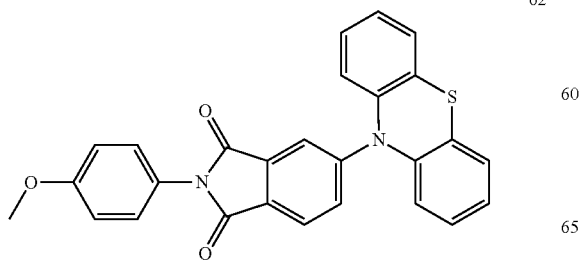
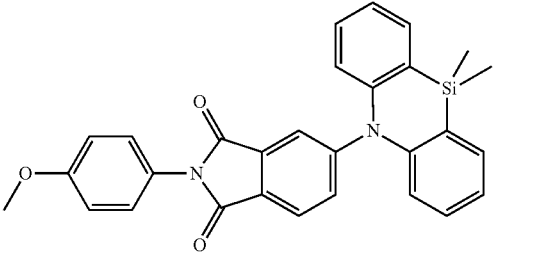
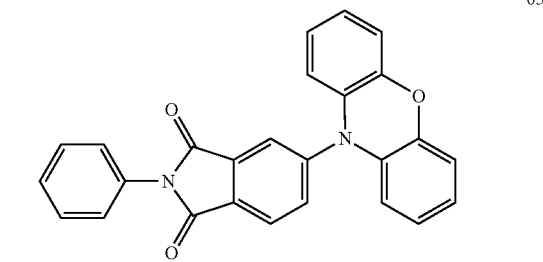
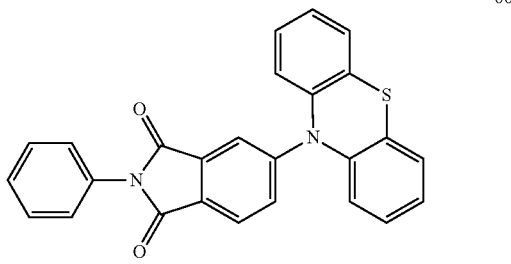
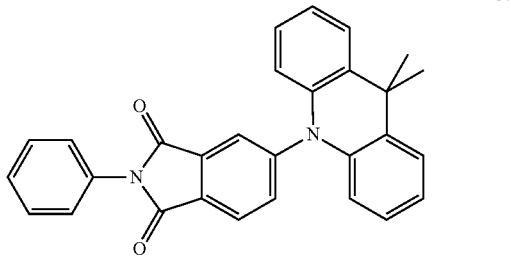
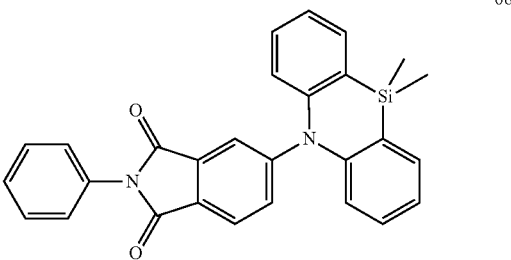

69
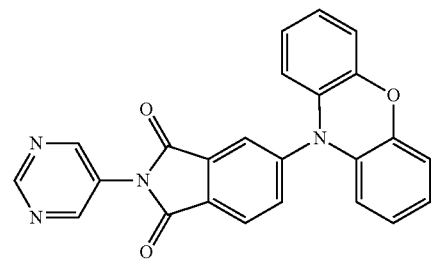
70
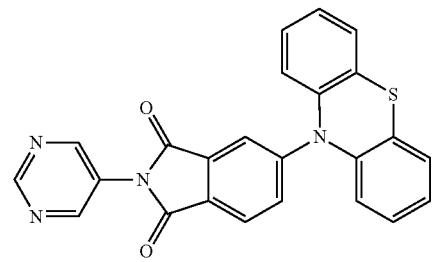
71
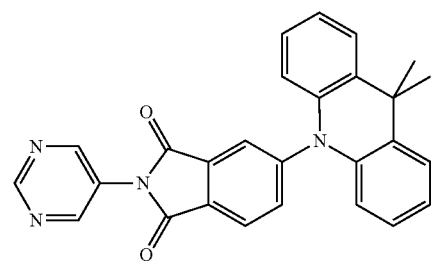
72
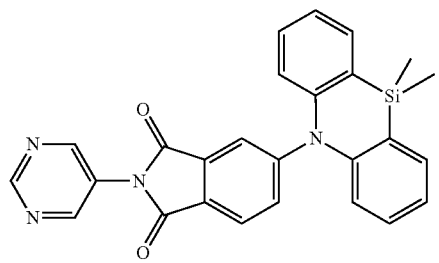
73
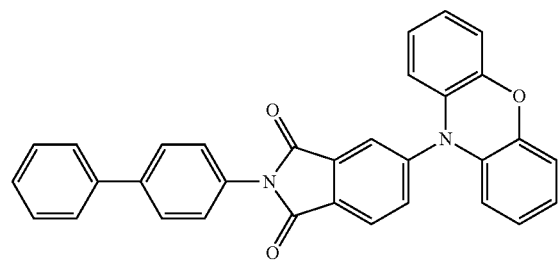
74
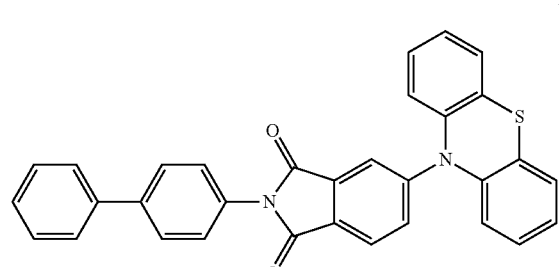
75
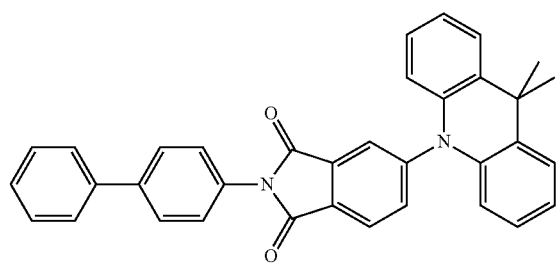
76
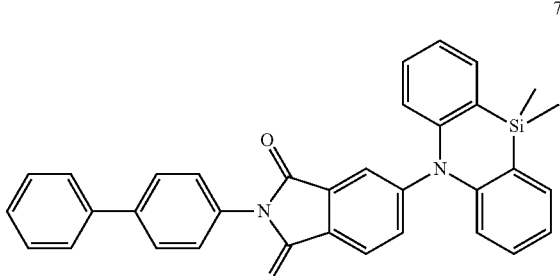
77
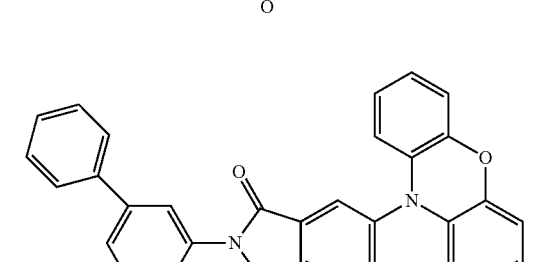
78
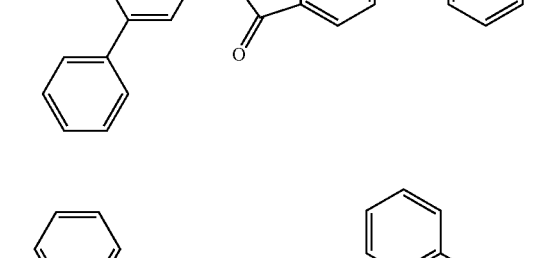
79
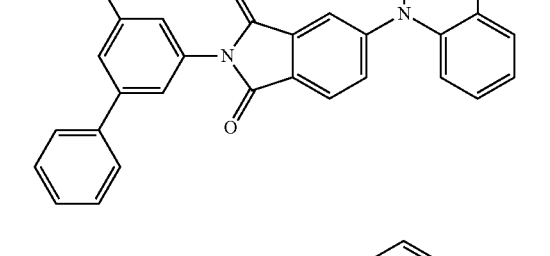
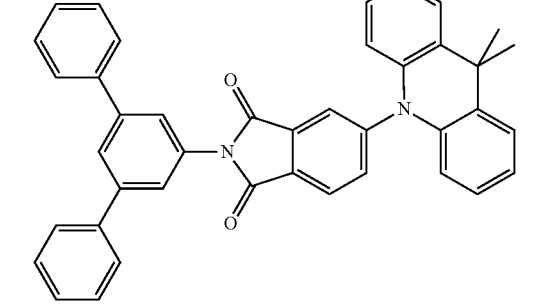

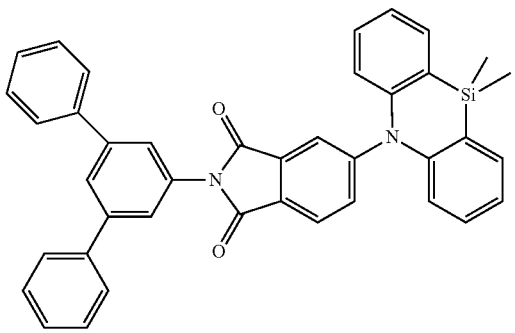

80

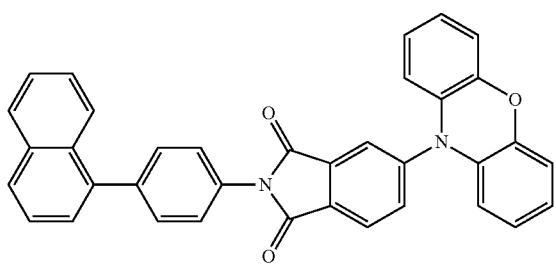

81

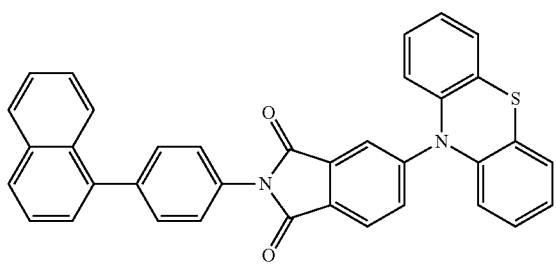

82

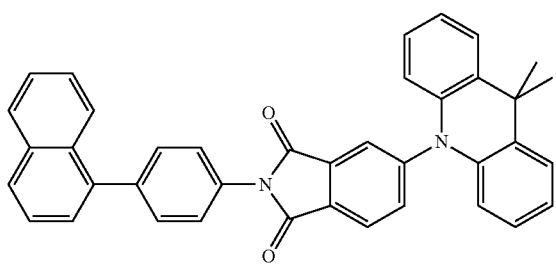

83

In one embodiment, the energy difference between the lowest singlet excited state ($S_1$) and the lowest triplet excited state ($T_1$) in the disclosed compounds may be configured to be $\Delta E_{st} \leq 0.30$ eV.

In another embodiment, the energy difference between the lowest singlet excited state ($S_1$) and the lowest triplet excited state ($T_1$) in the disclosed compounds may be configured to be $\Delta E_{st} \leq 0.25$ eV.

In another embodiment, the energy difference between the lowest singlet excited state ($S_1$) and the lowest triplet excited state ($T_1$) in the disclosed compounds may be configured to be $\Delta E_{st} \leq 0.20$ eV.

In another embodiment, the energy difference between the lowest singlet excited state ($S_1$) and the lowest triplet excited state ($T_1$) in the disclosed compounds may be configured to be $\Delta E_{st} \leq 0.15$ eV.

In another embodiment, the energy difference between the lowest singlet excited state ($S_1$) and the lowest triplet excited state ($T_1$) in the disclosed compounds may be configured to be $\Delta E_{st} \leq 0.10$ eV.

In another embodiment, the energy difference between the lowest singlet excited state ($S_1$) and the lowest triplet excited state ($T_1$) in the disclosed compounds may be configured to be $\Delta E_{st} \leq 0.05$ eV.

In another embodiment, the energy difference between the lowest singlet excited state ($S_1$) and the lowest triplet excited state ($T_1$) in the disclosed compounds may be configured to be $\Delta E_{st} \leq 0.02$ eV.

In another embodiment, the energy difference between the lowest singlet excited state ($S_1$) and the lowest triplet excited state ($T_1$) in the disclosed compounds may be configured to be $\Delta E_{st} \leq 0.01$ eV.

In the disclosed compounds, the energy difference between the lowest singlet excited state ($S_1$) and the lowest triplet excited state ($T_1$) may be configured to be $\Delta E_{st} = E_{S1} - E_{T1} \leq 0.30$ eV, or even less than or equal to 0.02 eV, such that the disclosed compounds may be used as TADF materials for the organic optoelectronic devices to improve the luminous efficiency. Moreover, the disclosed compounds may not contain expensive metal complexes, thereby reducing the manufacturing cost and widening the applications.

The present discourse also provides an organic optoelectronic device. The organic optoelectronic device may include an OLED, an organic solar cell, an organic photoelectric sensor, an organic storage device and any other appropriate organic optoelectronic devices. In one embodiment, the organic optoelectronic device may be an OLED. The OLED may include an anode, a cathode, and one or more organic thin film layers disposed between the anode and the cathode. At least one of the organic thin film layers may be a light-emitting layer, and the light-emitting layer may comprise any of the disclosed compounds of the present disclosure. The disclosed compound may be used as a dopant material, a co-doping material, or a host material in the light-emitting layer.

In certain embodiments, the OLED may also include at least one or a combination of at least two of a hole transport layer (HTL), a hole injection layer an electron blocking layer (EBL), a hole blocking layer (HBL), an electron transport layer (ETL), an electron injection layer (EIL). At least one of the hole transport layer (HTL), the hole injection layer (HIL), the electron blocking layer (EBL), the hole blocking layer (HBL), the electron transport layer (ETL), the electron injection layer (EIL) may comprise any of the disclosed compounds, in which the disclosed compound may be used as a dopant material, a co-doping material, or a host material.

FIG. 1 illustrates a schematic diagram of an exemplary OLED consistent with disclosed embodiments. As shown in FIG. 1, the OLED may include an anode 110 and a cathode 120 disposed on a substrate layer 100. At least a light-emitting layer 130 may be disposed between the anode 110 and the cathode 120. Other appropriate components may also be included. Electrons and holes may be recombined in the light-emitting layer 130, such that light is emitted from light-emitting layer 130.

Figure 2:
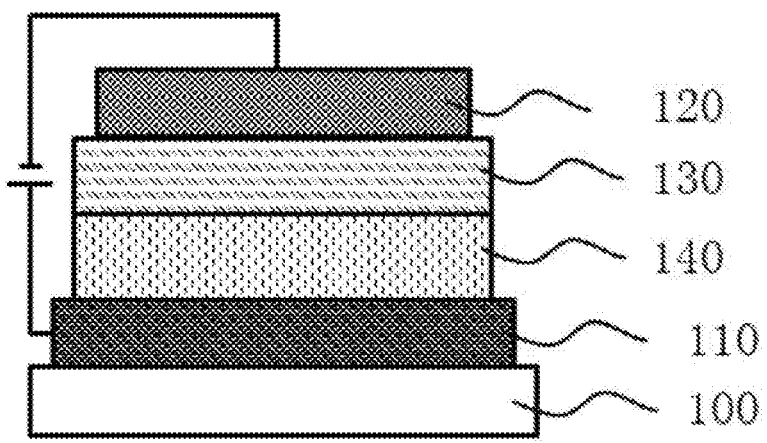
FIG. 2 illustrates a schematic diagram of another exemplary OLED consistent with disclosed embodiments.

FIG. 2 illustrates a schematic diagram of another exemplary OLED consistent with disclosed embodiments. The similarities between FIG. 1 and FIG. 2 are not repeated here, while certain difference may be explained. As shown in FIG. 2, a hole transport layer (HTL) 140 and a light-emitting layer 130 may be disposed between the anode 110 and the cathode

120. The hole transport layer (HTL) 140 may transfer the holes to the light-emitting layer 130.

Figure 3:
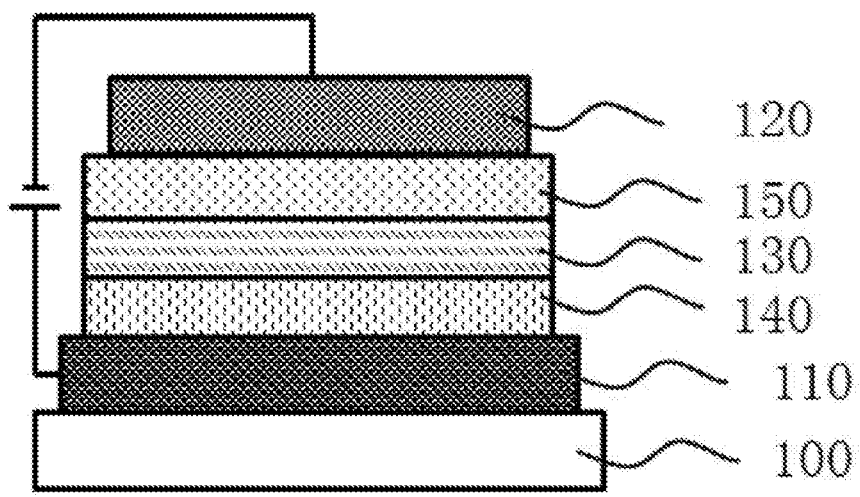
FIG. 3 illustrates a schematic diagram of another exemplary OLED consistent with disclosed embodiments.

FIG. 3 illustrates a schematic diagram of another exemplary OLED consistent with disclosed embodiments. The similarities between FIG. 1 and FIG. 3 are not repeated here, while certain difference may be explained. As shown in FIG. 3, a hole transport layer (HTL) 140, a light-emitting layer 130 and an electron transport layer (ETL) 150 may be disposed between the anode 110 and the cathode 120. The electron transport layer (ETL) 150 may transfer the electrons to the light-emitting layer 130.

Figure 4:
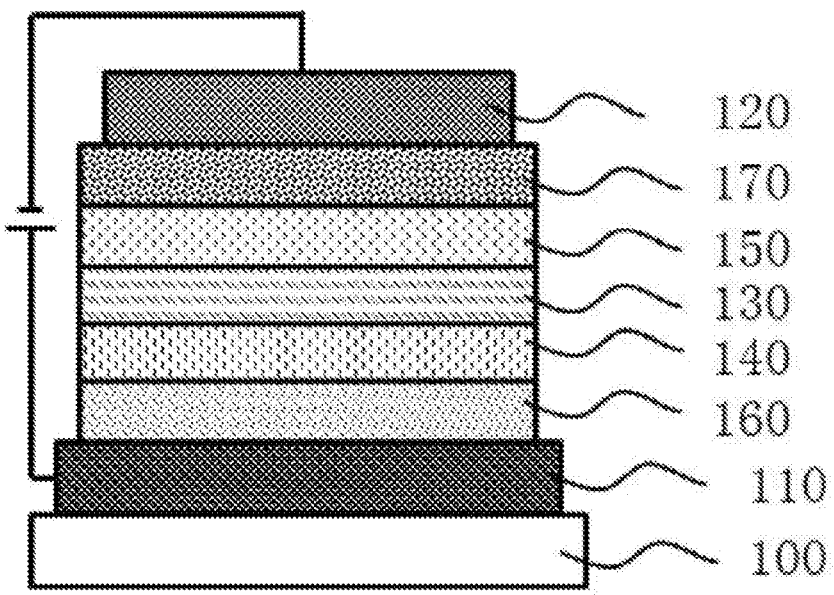
FIG. 4 illustrates a schematic diagram of another exemplary OLED consistent with disclosed embodiments.

FIG. 4 illustrates a schematic diagram of another exemplary OLED consistent with disclosed embodiments. The similarities between FIG. 1 and FIG. 4 are not repeated here, while certain difference may be explained. As shown in FIG. 4, a hole injection layer (HIL) 160, a hole transport layer 140, a light-emitting layer 130, an electron transport layer (ETL) 150, and an electron injection layer (EIL) 170 may be disposed between the anode 110 and the cathode 120. The hole injection layer (HIL) 160 may improve the ability to transfer holes from, the anode to the organic thin film layers. The electron injection layer (EIL) 170 may improve the ability to transfer electrons from the cathode to the organic thin film layers to reduce the driving voltage of the OLED.

Figure 5:
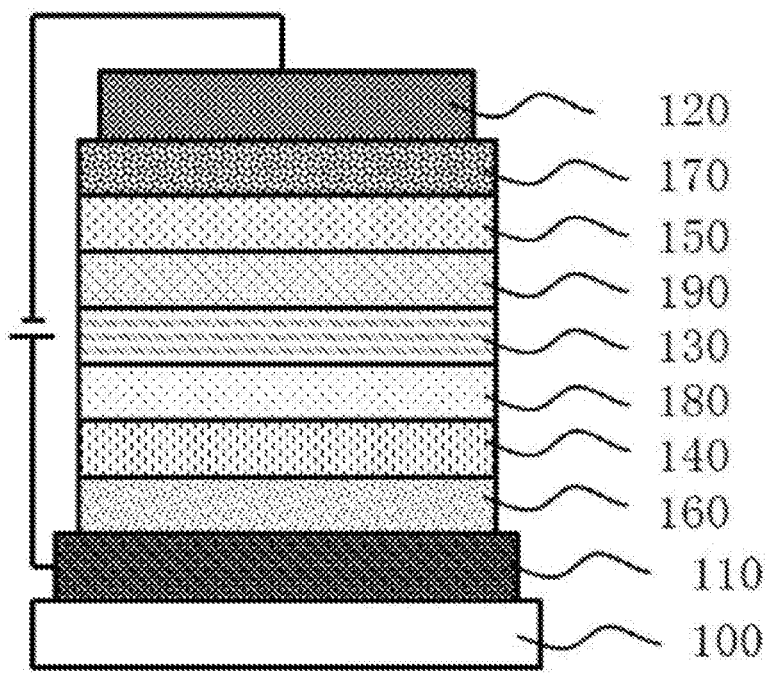
FIG. 5 illustrates a schematic diagram of another exemplary OLED consistent with disclosed embodiments.

FIG. 5 illustrates a schematic diagram of another exemplary OLED consistent with disclosed embodiments. The similarities between FIG. 1 and FIG. 5 are not repeated here, while certain difference may be explained. As shown in FIG. 5, a hole injection layer (HIL) 160, a hole transport layer (HTL) 140, an electron blocking layer (EBL) 180, a light-emitting layer 130, a hole blocking layer (HBL) 190, an electron transport layer (ETL) 150, and an electron injection layer (EIL) 170 may be disposed between the anode 110 and the cathode 120.

Materials of the anode, the cathode, and one or more organic thin film layers disposed between the anode and the cathode wilt be explained in detail, which are for illustrative purposes and are not intended to limit the scope of the present disclosure.

The anode 110 may be formed by an electrode material having a substantially large work function. The anode 110 may be firmed by metals or mixtures of, for example, copper, gold, silver, iron, chromium, nickel, manganese, palladium, platinum. The anode 110 may be formed by metal alloys, for example, copper, gold, silver, iron, chromium, nickel, manganese, palladium or platinum. The anode 110 may be formed by metal oxides or mixture of, for example, indium oxide, zinc oxide, indium tin oxide (ITO), indium zinc oxide (IZO). The anode 110 may be formed by the conductive polymers or mixtures of, for example, polyaniline, polypyrrole, poly (3-methylthiophene). In the disclosed embodiments, the anode may be formed by indium tin oxide (ITO).

The cathode 120 may be formed by an electrode material having a low work function. The cathode 120 may be formed by metals or mixtures of, for example, aluminum, magnesium, silver, indium, tin, titanium, calcium, sodium, potassium, lithium, ytterbium, lead. The cathode 120 may also be formed by multi-layer metal materials, such as LiF/Al, Liq (8-hydroxyquinoline)/Al or a mixture thereof. In the disclosed, embodiments, the cathode 120 may be formed by a magnesium silver alloy or a LiF/Al double layer material.

The hole injecting layer (HIL) 160 may be formed by a material, which may facilitate the hole injection at the interface between the anode and the organic film layer and, meanwhile, may be well bonded to the surface of the ITO anode. The material forming the hole injecting layer (HIL) 160 may include, for example, copper phthalocyanine (CuPc) polyporphyrin compounds such as 4,4', 4"-tri-N-naphthyl-N-anilino-triphenylamine (TNATA), poly (3,4-ethylenedioxythiophene); polystyrene sulfonate (PEDOT: PSS) having an HOMO level matching the work function of ITO, 2,3,6,7,10,11-hexacyanoyl-1,4,5,8,9,12-hexaazahenzophenanthrene (HATCN), electron-withdrawing N-heterocyclic compounds such as 2,3,6,7,10,11-hexacyanoyl-1,4,5, 8,9,12-hexaazabenzophenanthrene (HATCN).

The hole transport layer (HTL) 140 and the electron blocking, layer (EBL) 180 may be formed by a material having a high glass transition temperature and a high hole mobility. Materials used as the hole transport layer (HTL) 140 and the electron blocking layer (EBL) 180 may include biphenyl diamine derivatives such as diphenylnaphthylenediamine (NPD), crosslinked diamine biphenyl derivatives such as 2,2', 7,7'-tetrakis (diphenylamino)-9,9'-spirobifluourene (spiro-TAD), stellate, triphenylamine derivatives such as 4',4"-tris(N-carbazolyl) triphenylamine (TCTA).

The hole blocking layer (HBL) 190 and the electron transport layer (ETL) 150 may be formed by a material having a low HOMO level and high electron mobility. Materials used as the hole blocking layer and the electron transport layer may include quinoline metal complexes such as bis (8-hydroxy-2-methylquinoline)-diphenol aluminum (BAlq), tris (8-quinolinolato) aluminum (Alq), 8-hydroxyquinoline lithium, phenanthroline derivatives such as 4,7-diphenyl-1,10-phenanthroline (Bphen), imidazole derivatives such as 1,3,5,3-tris (N-phenyl-benzimidazol-2-yl) benzene (TPBI), and triazine derivatives such as 2,4,6-tricarbazolyl-1,3,5-triazine.

Figure 6:
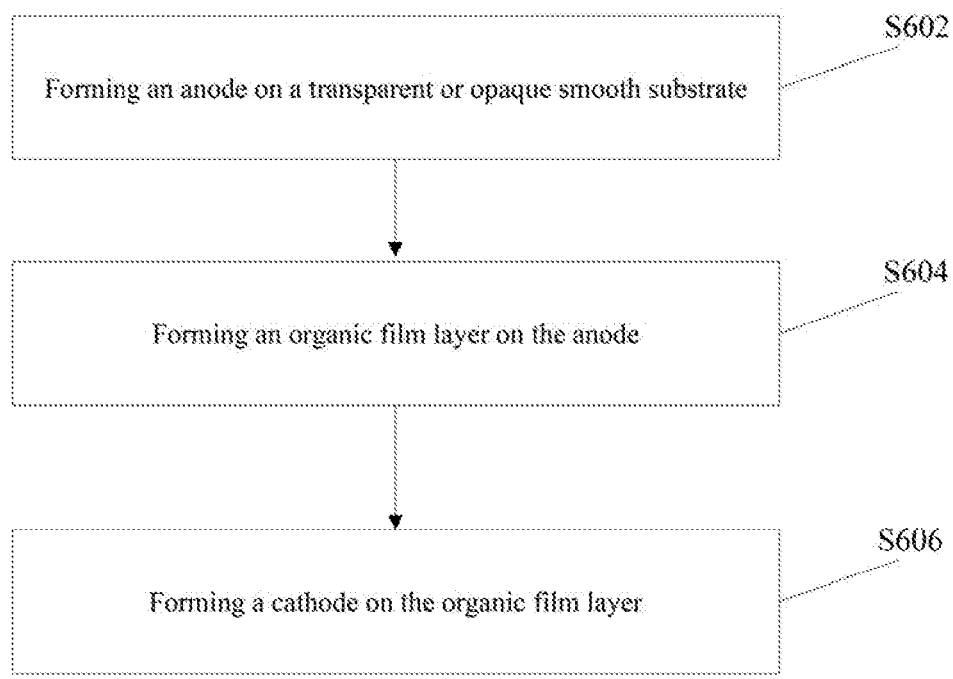
FIG. 6 illustrates a flow chart of an exemplary OLED fabrication method consistent with disclosed embodiments.

FIG. 6 illustrates a flow chart of an exemplary OLED fabrication method consistent with disclosed embodiments. As shown in FIG. 6, the OLED may be fabricated by forming an anode on a transparent or opaque smooth substrate (S602), forming an organic film layer on the anode (S604), and forming a cathode on the organic film layer (S606). The organic film layer may be formed by an existing method, such as vapor deposition, sputtering, spin coating, dipping, or ion plating.

The preparation of the certain disclosed Compounds will be explained as follows, which is for illustrative purposes and is not intended to limit the scope of the present disclosure. The disclosed compounds may be prepared in other appropriate methods.

Example 1

Preparation of Compound 1

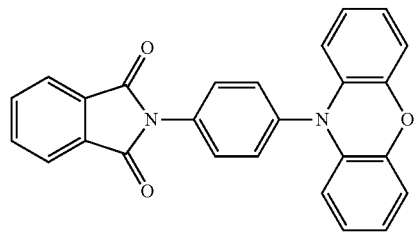

Compound 1

Example 2

Preparation of Compound 5

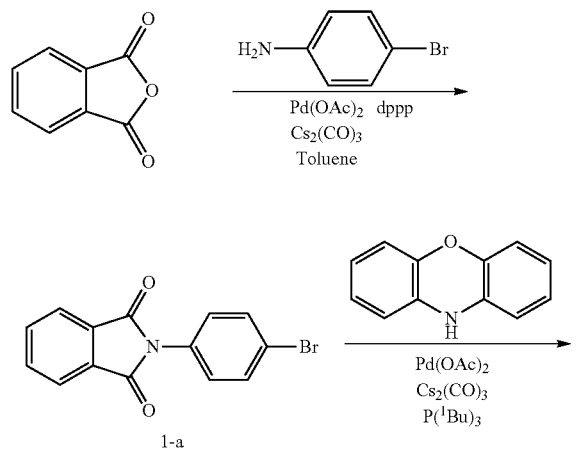

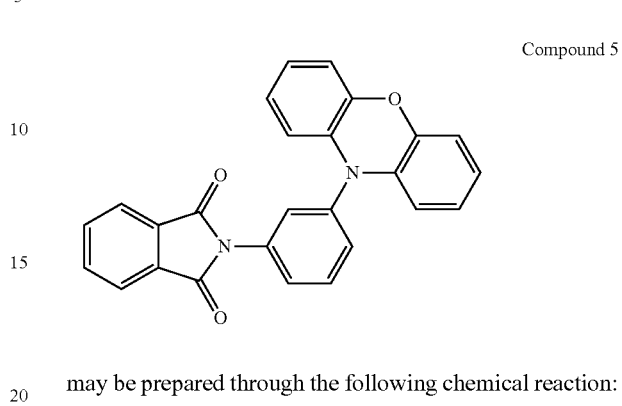

may be prepared through the following chemical reaction:

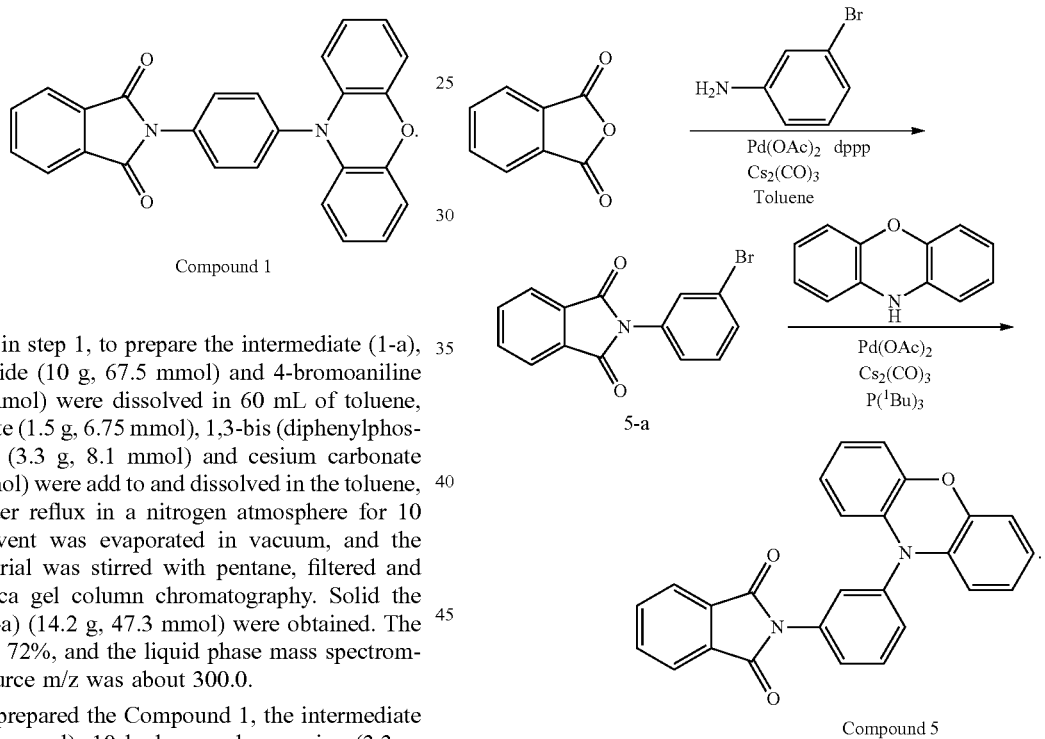

In particular, in step 1, to prepare the intermediate (1-a), phthalic anhydride (10 g, 67.5 mmol) and 4-bromoaniline (12.1 g, 70.8 mmol) were dissolved in 60 mL of toluene, palladium acetate (1.5 g, 6.75 mmol), 1,3-bis (diphenylphosphino) propane (3.3 g, 8.1 mmol) and cesium carbonate (47.1 g, 135 mmol) were add to and dissolved in the toluene, and heated under reflux in a nitrogen atmosphere for 10 hours. The solvent was evaporated in vacuum, and the remaining material was stirred with pentane, filtered and purified by silica gel column chromatography. Solid the intermediate (1-a) (14.2 g, 47.3 mmol) were obtained. The yield was about 72%, and the liquid phase mass spectrometer ESI ion source m/z was about 300.0.

In step 2, to prepared the Compound 1, the intermediate (1-a) (5 g, 16.5 mmol), 10 hydrogen-phenoxazine (3.3 g, 18.15 mmol), palladium acetate (0.4 g, 1.98 mmol) cesium carbonate (11.5 g, 33 mmol) and tert-butylphosphine (0.5 g, 2.4 mmol) were dissolved in toluene and refluxed for 5 hours. The toluene was dried in vacuum, and the solid was dissolved in ethyl acetate, stirred, filtered and washed three times with saturated brine. Then the solvent was evaporated under vacuum steaming. The solid was purified by silica gel column chromatography, and solid Compound 1 (3.6 g. 8.9 mmol) was obtained. The yield was about 54% yield, and the liquid phase mass spectrometer ESI ion source m/z was about 402.1.

The disclosed Compounds 2-4 may be synthesized in a manner similar as the Compound 1, except that in the step 2, 10 hydrogen-phenoxazine may be replaced by 9,9-dimethylacridine, 10 hydrogen-phenothizine, and 10, 10-dimethyl-5-hydro-phenyene silane, respectively.

In particular, in step 1, to prepare the intermediate (5-a), phthalic anhydride (10 g, 67.5 mmol) and 3-bromoaniline (12.1 g, 70.8 mmol) were dissolved in 60 mL of toluene, Palladium acetate (1.5 g, 6.75 mmol), 1,3-bis (diphenylphosphino) propane (3.3 g, 8.1 mmol) and cesium carbonate (47.1 g, 135 mmol) were add to and dissolved in the toluene, and heated under reflux in a nitrogen atmosphere for 10 hours. The solvent was evaporated in vacuum, and pentane was added to the remaining material, and the mixture was stirred, filtered and purified by silica, gel column chromatography. Solid compound (5-a) (13.5 g, 45 mmol) was obtained. The yield was about 68%, and the liquid phase mass spectrometer ESI ion source m/z was about 301.1.

In step 2, to prepared the Compound 5, the intermediate (5-a) (5 g, 16.5 mmol), 10 hydrogen-phenoxazine (3.3 g, 18.15 mmol), palladium acetate 40.4 g, 1.98 mmol), cesium carbonate (11.5 g, 33 mmol) and tert-butylphosphine (0.5 g, 2.4 mmol) were dissolved in toluene and refluxed for 5 hours. The toluene was dried in vacuum, and the solid was dissolved in ethyl acetate, stirred, filtered and washed three times with saturated brine. Then the solvent was evaporated under vacuum steaming, and the solid was purified by silica gel column chromatography. Then solid Compound 5 (4.3 g, 0.6 mmol) was obtained. The yield was about 64% yield, and the liquid phase mass spectrometer ESI ion source m/z was about 402.1.

The disclosed Compounds 6-8 may be synthesized in a manner similar as the Compound 5, except that in the step 2, 10 hydrogen-phenoxazine may be replaced by 9,9-dimethylacridine, 10 hydrogen-phenothiazine, and 10, 10-dimethyl-5-hydro-phenylene silane, respectively.

The disclosed Compounds 9-12 may be synthesized in a manner similar as the Compounds 1-4, except that in the step 1, phthalic anhydride may be replaced by 4-phenylphthalic anhydride.

The disclosed Compounds 13-16 may be synthesized in a manner similar as the Compounds 9-12, except that in the step 1, 4-bromoaniline may be replaced by 3-bromoaniline.

The disclosed Compounds 17, 18, 28, 29 may be synthesized in a manner similar as the Compounds 1-4, except that in the step 1,4-bromobenzene is replaced by 3,5-dibromo-biphenyl.

The disclosed Compounds 19-22 may be synthesized in a manner similar as the Compounds 1-4, except that in the step 1, phthalic anhydride may be replaced by 4,5-diphenyl-phthalic anhydride.

The disclosed Compounds 23-26 may be synthesized in a manner similar as the Compounds 19-22, except that in the step 1, 4-bromoaniline may be replaced by 3-bromoaniline.

Example 3

Preparation of Compound 30

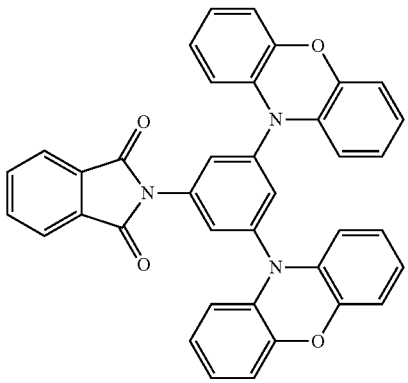

Compound 30 may be prepared through the following chemical reaction:

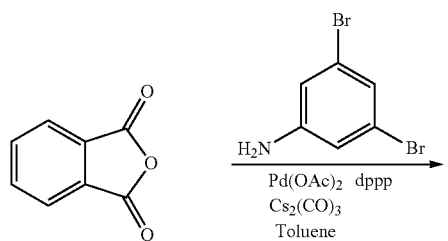

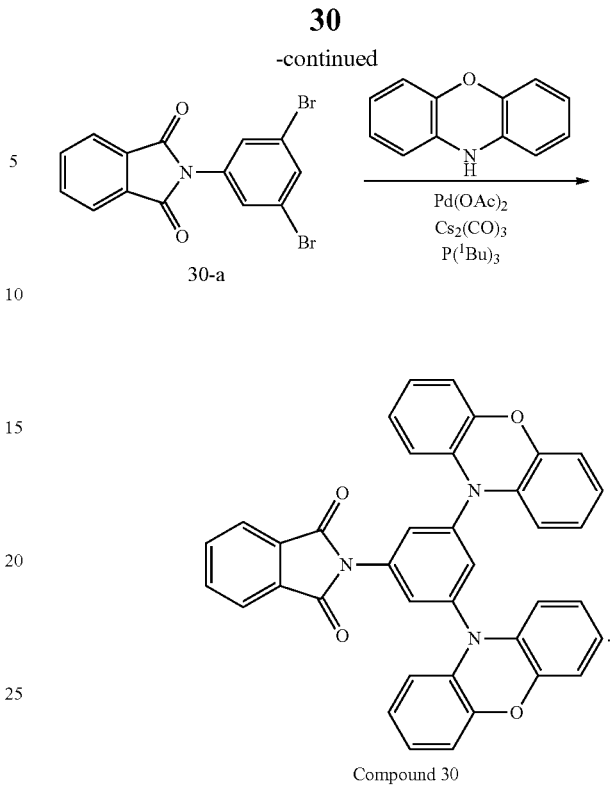

In particular, in step 1, to prepare the intermediate (30-a), phthalic anhydride (10 g, 67.5 mmol) and 3,5-dibromoaniline (18.1 g. 72.0 mmol were dissolved in 80 mL of toluene. Palladium acetate (1.5 g, 6.75 mmol), (diphenylphosphino) propane (3.3 g. 8.1 mmol) and cesium carbonate (47.1 g, 135 mmol) were add to and dissolved in the toluene, and heated under reflux for 8 hours under a nitrogen atmosphere. The solvent was evaporated in vacuum, and pentane was added to the remaining material, and the mixture was stirred, filtered and purified by silica gel column chromatography. Solid compound (30-a) (17.14 g, 45 mmol) was obtained. The yield was about 72%, and the liquid phase mass spectrometer ESI ion source m/z was about 380.9.

In step 2, to prepared the Compound 30, the intermediate (30-a) (5 g, 16.5 mmol), 10 hydrogen-phenoxazine (3.3 g, 18.15 mmol), palladium acetate (0.5 g, 2.50 mmol), cesium carbonate (11.5 g, 33 mmol) and tert-butylphosphine (0.5 g, 2.4 mmol) were dissolved in toluene and refluxed for 8 hours. The toluene was dried in vacuum, and the solid was dissolved in ethyl acetate, stirred, filtered and washed three times with saturated brine. Then the solvent was evaporated under vacuum steaming, and the solid was purified by silica gel column chromatography. Solid Compound 30 (5.26 g, 9.0 mmol) was obtained. The yield was about 55% yield, and the liquid phase mass spectrometer ESI ion source m/z was about 585.2.

The disclosed Compounds 31 and 35 may be synthesized in a manner similar as the Compound 30, except that in the step 2, 10 hydrogen-phenoxazine may be replaced by 10 hydrogen-phenothiazine and 9,9-dimethylacridine, respectively.

Example 4

Preparation of Compound 32

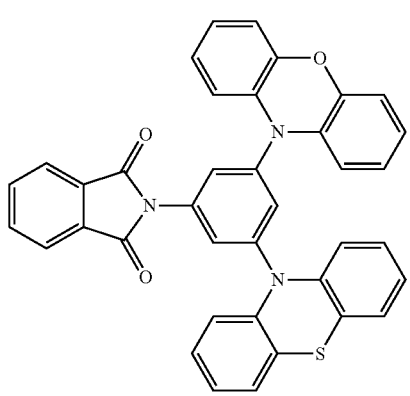

Compound 32 may be prepared through the following chemical reaction:

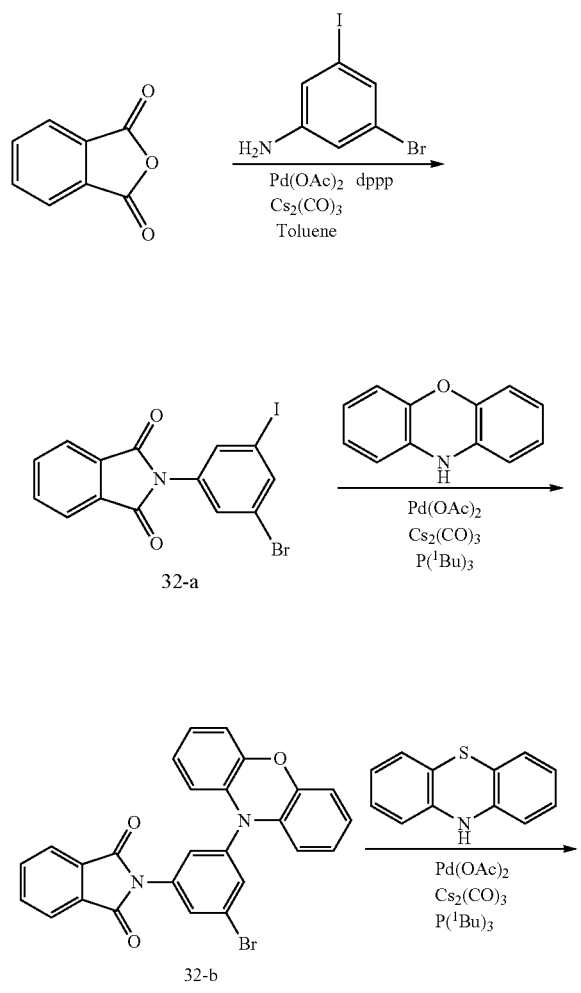

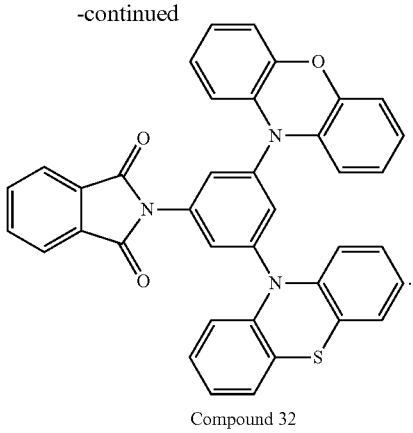

Compound 32

In particular, in step 1, to prepare the intermediate (32-a), phthalic anhydride (10 g, 67.5 mmol) and 3-bromo-5-iodoaniline (20.8 g, 70 mmol) wore dissolved in 80 mL of toluene. Palladium acetate (1.5 g, 6.75 mmol), 1,3-bis (diphenylphosphino) propane (3.3 g, 8.1 mmol) and cesium carbonate (47.1 g, 135 mmol) were add to and dissolved in the toluene, and heated under reflux in a nitrogen atmosphere for 10 hours. The solvent was evaporated in vacuum, and pentane was added to the remaining material, and the mixture was stirred, filtered and purified by silica gel column chromatography. Solid compound (32-a) (18.4 g, 43.0 mmol) was obtained. The yield was about 64%, and the liquid phase mass spectrometer ESI ion source m/z was about 426.9.

In step 2, to prepare the intermediate (32-b), compound (32-a) (6.4 g 15.0 mmol), palladium (0.5 g, 2.50 mmol), cesium carbonate (11.5 g, 33 mmol) and tert-butylphosphine (0.5 g, 2.4 mmol) were dissolved in toluene and refluxed for 6 hours. The toluene was dried in vacuum and the solid was dissolved in ethyl acetate, stirred, filtered and washed three times with saturated brine. The solvent was evaporated under vacuum steaming, and the remaining materials were purified by silica gel column chromatography. Solid compound (32-b) (4.11 g, 8.5 mmol) was obtained. The yield was about 59%, and the liquid phase mass spectrometer ESI ion source m/z was about 484.0.

In step 3, to prepare the Compound 32, compound (32-b) (4.84 g, 1.0 mmol), 10 hydrogen-phenothiazine (2.59 g, 13 mmol), palladium (0.5 g, 2.50 mmol), cesium carbonate (11.5 g, 33 mmol) and tert-butylphosphine (0.5 g, 2.4 mmol) were added to a solution of the compound (4.84 g, 10 mmol), 10 hydrogen-phenothiazine (2.59 g, 13 mmol) were dissolved in toluene, refluxed and stirred for 6 hours. The toluene was dried in vacuum and the solid was dissolved in ethyl acetate, stirred, filtered and washed three times with saturated brine. The solvent was evaporated under vacuum steaming, and the remaining materials were purified by silica gel column chromatography. Solid compound 32 (3.0 g, 5.0 mmol) was obtained. The yield was about 5%, and the liquid phase mass spectrometer ESI ion source m/z was about 601.1.

The disclosed Compounds 33 and 36 may be synthesized in a manner similar as the Compound 32, except that in the step 3, 10 hydrogen-phenothiazine may be replaced by 9,9-dimethylacridine and 10,10-dimethyl-5-hydro-phenylene silane, respectively.

The disclosed Compounds 34 and 37 may be synthesized in a manner similar as the Compound 32, except that, in the step 2, 10 hydrogen-phenoxazine may be replaced by 10 hydrogen-phenothiazine, and in the step 3, 10 hydrogen-phenothiazine may be replaced by 9-dimethylacridine and 10,10-dimethyl-5-hydro-phenylene respectively.

The disclosed Compound 38 may be synthesized in at manner similar as the Compound 32, except that, in the step 2, 10 hydrogen-phenoxazine may be replaced by 10 dimethyl-5-hydro-phenylene silane, and in the step 3, 10 hydrogen-phenothiazine may be replaced by 9,9-dimethylacridine.

The disclosed Compound 39 may be synthesized in a manner similar as the Compound 1, except that, in the step 1, 4-bromoaniline was replaced by 5-bromo-3-methoxyaniline.

The disclosed Compounds 40-42 may be synthesized in a manner similar as the Compound 39, except that, in the step 2, 10 hydrogen-phenoxazine may be replaced by 9,9-dimethylacridine, 10 hydrogen-phenothiazine, 10,10-dimethyl-5-hydro-phenylene silane, respectively.

Example 5

Preparation of Compound 43

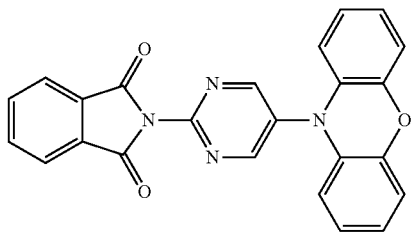

Compound 43 may be prepared through the following chemical reaction:

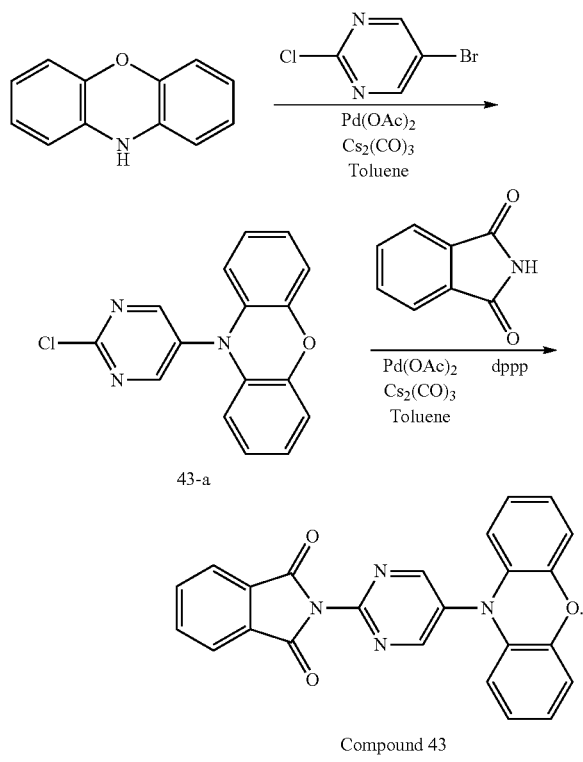

Compound 43

In particular, in step 1, to prepare the intermediate (43-a), 10 hydrogen-phenoxazine (3.3 g, 18.15 mmol), 2-chloro-5-bromo-pyrimidine (3.2 g, 16.5 mmol), palladium acetate (0.4 g, 1.98 mmol), cesium carbonate (11.5 g, 33 mmol) and tert-butylphosphine (0.5 g, 2.4 mmol) were dissolved in toluene and refluxed for 5 hours. The toluene was dried in vacuum and the solid was dissolved in ethyl acetate, stirred, filtered and washed three times with saturated brine. The solvent was evaporated in vacuum steaming, and the remaining material was purified by silica, gel column chromatography. Solid compound (43-a) (32 g, 10.8 mmol) was obtained. The yield was about 65%, and the liquid phase mass spectrometer ESI ion source m/z was about 295.1.

In step 2, to prepare the Compound 43, phthalimides (8.8 g, 60 mmol) and compound (43-a) (14.8 g, 50 mmol) were dissolved in 60 mL of toluene. Then palladium acetate (1.5 g, 6.75 mmol), 1,3-bis (diphenylphosphine) propane (3.3 g, 8.1 mmol) and cesium carbonate (47.1 g, 135 mmol) were added to and dissolved, in the toluene, and heated under reflux in a nitrogen atmosphere for 10 hours. The solvent was evaporated in vacuum, and pentane was added to the remaining material, and the mixture was stirred, filtered and purified by silica gel column chromatography, Solid Compound 43 (11.4 g, 28.0 mmol) was obtained. The yield was about 47%, and the liquid phase mass spectrometer ESI ion source m/z was about 406.1.

The disclosed Compounds 44-46 may be synthesized in a manner similar as the Compound 43, except that, in the step 1, 10 hydrogen-phenoxazine may be replaced by 9,9-dimethylacridine, 10 hydrogen-phenothiazine, and 10,10-dimethyl-5-hydro-phenylene silane, respectively.

The disclosed Compounds 47, 48, 50 and 51 may be synthesized in a manner similar as the Compound 43 except that, in the step 1, 10 hydrogen-phenoxazine may be replaced by 9,9-dimethylacridine, 10 hydrogen-phenothiazine, 10,10-dimethyl-5-hydro-phenylene silane, and in the step 2, phthalimide may be replaced by 4-methoxy-1,2-phthalimide.

The disclosed Compound 49 may be synthesized in a manner similar as the Compound 51, except that, in the step, 2-chloro-5 bromo-pyrimidine may be replaced by 2-chloro-4-bromo-pyrimidine.

The disclosed Compound 54 may be synthesized in a manner similar as the Compound 43, except that in the step 2, phthalimide may be replaced by 4-methoxy-1,2-phthalimide.

The disclosed Compounds 52, 53, 55 may be synthesized in a manner similar as the Compound 54, except that, in the step 1, 10 hydrogen-phenoxazine may be replaced by 9,9-dimethylacridine, 10 hydrogen-phenothiazine, and 10,10-dimethyl-5-hydro-phehylene silane.

The disclosed Compounds 56, 57, 59 and 60 may be synthesized in a manner similar as the Compound 52, 53, 54 and 55, except that, in the step 2, phthalimide may be replaced by 4-(1, -naphthyl)-phthalimide.

Example 6

Preparation of Compound 61

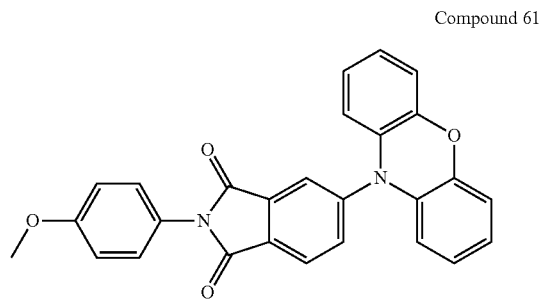 [SMILES: COc1ccc(N2C(=O)c3ccc(N4c5ccccc5Oc5ccccc54)cc3C2=O)cc1]

Compound 61 may be prepared through the following chemical reaction:

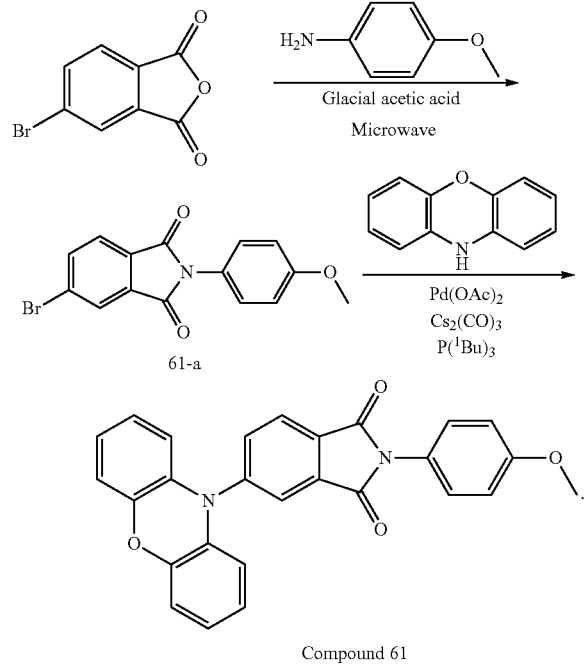

Compound 61

In particular, in step 1, to prepare the intermediate (61-a), 4-bromophthalic anhydride (10 g, 44.0 mmol) and p-methoxyaniline (6.5 g, 52.8 mmol) were dissolved in 10 mL of glacial acetic acid, and a number of molecular sieves were also added to the glacial acetic acid and heated in a microwave at 120° C. for 1 hour. The reaction solvent was neutralized with sodium hydroxide in ice water, extracted with dichloromethane, and dried over anhydrous magnesium sulfate. The solvent was evaporated in vacuum and the remaining material was purified by silica gel column chromatography. Solid compound (61-a) (11.6 g, 35.2 mmol) was obtained. The yield was about 80%, and the liquid phase mass spectrometer ESI ion source m/z was about 332.1.

In step 2, to prepare the Compound 61, compound (61-a) (5 g. 15.0 mmol), 10 hydrogen-phenoxazine (10 g, 16.5 mmol), palladium acetate (0.3 g, 0.15 mmol), cesium carbonate (10.5 g, 30 mmol) and t-butylphosphine ((14 g, 1.8 mmol) were dissolved in 20 mL of toluene, refluxed and stirred for 5 hours. The toluene was dried in vacuum and the solid was dissolved in ethyl acetate, stirred, filtered and washed three times with saturated water. The solvent was evaporated, and Compound 61 (3.9 g, 8.95 mmol) was obtained. The yield was about 60%, and the liquid phase mass spectrometer ESI ion source m/z was about 433.8.

The disclosed Compounds 62-64 may be synthesized in a manner similar as the Compound 61, except that, in the step 2, 10 hydrogen-phenoxazine may be replaced by 9,9-dimethylacridine, 10 hydrogen-phenothiazine, and 10,10-dimethyl-5-hydrogen-phenylene silane, respectively.

Example 7

Preparation of Compound 65

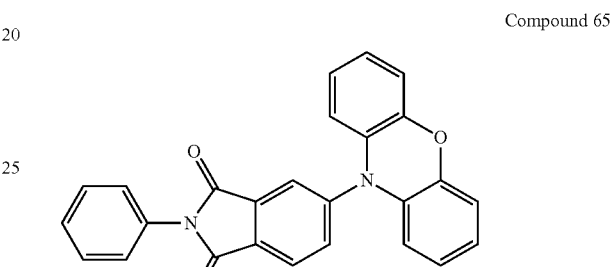

Compound 65 may be prepared through the following chemical reaction:

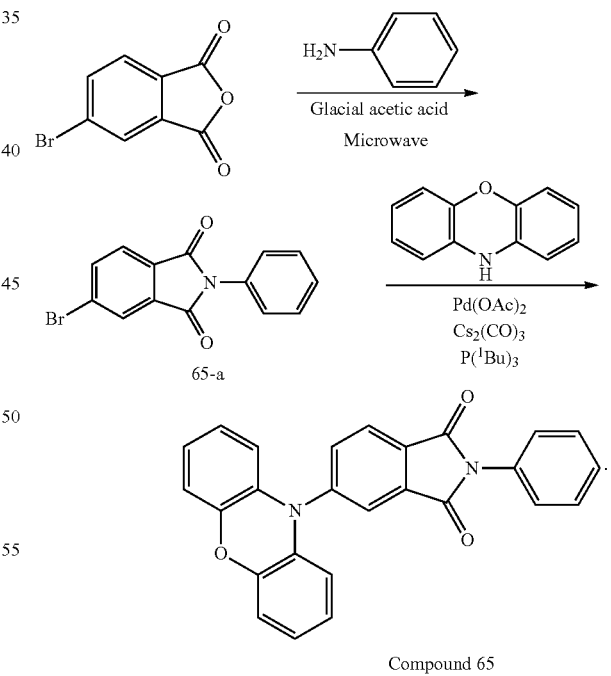

Compound 65

In particular, in step 1, to prepare the intermediate (65-a), 4-bromophthalic anhydride (10 g, 44.0 mmol) and aniline (4.9 g, 52.8 mmol) were dissolved in 10 mL of glacial acetic acid, and a number of molecular sieves were also added to the glacial acetic acid and heated in a microwave at 120° C. for 1 hour. The reaction solvent was neutralized with sodium hydroxide in ice water, extracted with dichloromethane, and dried over anhydrous magnesium sulfate. The solvent was evaporated in vacuum, and the remaining material was purified by silica gel column chromatography. Solid compound (65-a) (11.4 g, 38 mmol) was obtained. The yield was about 86%, and the liquid phase mass spectrometer ESI ion source m/z was about 301.

In step 2, to prepare the Compound 65, compound (65-a) (4.5 g. 15.0 mmol), 10 hydrogen-phenoxazine (3.0 g 16.5 mmol), palladium acetate (0.3 g. 0.15 mmol), cesium carbonate (10.5 g, 30 mmol) and t-butylphosphine (0.4 g. 1.8 mmol) were dissolved in 20 mL of toluene, refluxed and stirred for 5 hours. The toluene was dried in vacuum and the solid was dissolved in ethyl acetate, stirred, filtered and washed three times with saturated water. The solvent was evaporated, and Compound 65 (4.5 g, 11.13 mmol) was obtained. The yield was about 74%, and the liquid phase mass spectrometer ESI ion source m/z was about 404.1.

The disclosed Compounds 66-68 may be synthesized in a manner similar as the Compound 65, except that, in the step 2, 10 hydrogen-phenoxazine may be replaced by 9,9-dimethylacridine, 10 hydrogen-phenothiazine, and 10,10-dimethyl-5-hydrogen-phenylene silane, respectively.

The disclosed Compounds 69-72 may be synthesized in a manner similar as the Compound 65, except that, in the step 1, aniline may be replaced by 5-aminopyrimidine.

Example 8

Preparation of Compound 73

Compound 73

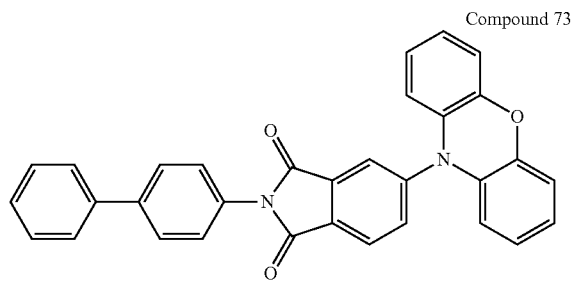 [SMILES: O=C1c2ccc(N3c4ccccc4Oc4ccccc43)cc2C(=O)N1c1ccc(-c2ccccc2)cc1]

may be prepared through the following chemical reaction:

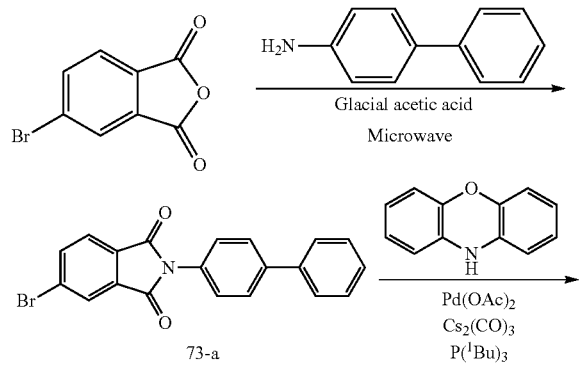

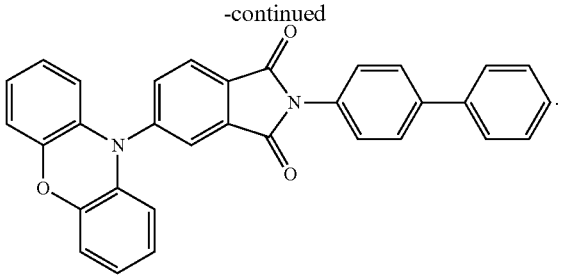

Compound 73

In particular, in step 1, to prepare the intermediate (73-a), 4-bromophthalic anhydride (10 g, 44.0 mmol) and 4-aminobiphenyl (8.5 g, 50.3 mmol) were dissolved in 10 mL of glacial acetic acid, and a number of molecular sieves were also added to the glacial acetic acid and heated in a microwave at 120° C. for 1 hour. The reaction solvent was neutralized with sodium hydroxide in ice water, extracted with dichloromethane, and dried over anhydrous magnesium sulfate. The solvent was evaporated in vacuum, and the remaining material was purified by silica gel column chromatography. Solid compound (73-a) (13.3 g, 35.1 mmol) was obtained. The yield was about 80%, and the liquid phase mass spectrometer ESI ion source m/z was about 379.

In step 2, to prepare the Compound 73, compound (73-a) (5.6 g, 15.0 mmol), 10 hydrogen-phenoxazine (3.0 g, 16.5 mmol), palladium acetate (0.3 g, 0.15 mmol), cesium carbonate (10.5 g, 30 mmol) and t-butylphosphine (0.4 g, 1.8 mmol) were dissolved in 20 mL of toluene, refluxed and stirred for 5 hours. The toluene was dried in vacuum and the solid was dissolved in ethyl acetate, stirred, filtered and washed three times with saturated water. The solvent was evaporated, and Compound 73 (4.6 g, 9.6 mmol) was obtained. The yield was about 64%, and the liquid phase mass spectrometer ESI ion source m/z was about 480.1.

The disclosed Compounds 74-76 may be synthesized in a manner similar as the Compound 65, except that, in the step 2, 10 hydrogen-phenoxazine may be replaced by 9,9-dimethylacridine, 10 hydrogen-phenothiazine, and 10,10-dimethyl-5-hydrogen-phenylene respectively.

The disclosed Compounds 77-80 may be synthesized in a manner similar as the Compounds 74-76, except that, in the step 1, 4-aminobiphenyl may be replaced by 3,5-diphenylanilineaniline.

The disclosed Compounds 27, and 81-83 may be synthesized in a manner similar as the Compounds 74-76, except that, in the step 1, 4-aminobiphenyl may be replaced by 4-(1, -naphthyl)

The other disclosed compounds may be synthesized in a similar manner, which is not repeated here.

Example 9

Simulation of Compounds

The energy difference between single and triplet states of the disclosed compounds may be obtained by Guassian 09 software (Guassian Inc.). The energy difference ΔEst may be simulated according to the simulation method described Chem. Theory Comput., 2013 (DOI: 10.1021/ct400415r). The molecular structure optimization and molecular excitation may be performed by using the TD-DFT method "B3LYP" and the base group "6-31 g (d)". For illustrative purposes, a simulation is performed for the Compounds 1, 2, 43, 63 and 64 selected from the compounds 1-83. The simulation results of the Compounds 1, 2, 43, 63 and 64 are shown in Table 1.

TABLE 1

Simulation results of five exemplary compounds

| Compound | $S_1$(eV) | $T_1$(eV) | $\Delta E_{st}$(eV) |
|---|---|---|---|
| 1 | 2.4202 | 2.4198 | 0.004 |
| 2 | 2.8224 | 2.8221 | 0.003 |
| 43 | 2.9430 | 2.6681 | 0.2749 |
| 63 | 2.4585 | 2.4421 | 0.0164 |
| 64 | 2.5982 | 2.5827 | 0.0155 |

As shown in Table 1, the energy difference between single and triplet states of disclosed compounds are substantially small, which may enable efficient reverse intersystem crossing (RISC) in the compounds and provide TADF properties. Thus, the disclosed compounds may have a heat activated delayed fluorescence (TADF) material luminescence mechanism, which may be used as a new type of TADF material in the organic optoelectronic devices to improve the luminous efficiency. Moreover, the disclosed compounds may be prepared without expensive metal complexes, thereby reducing the manufacturing cost and widening the applications.

Example 10

Organic Optoelectronic Device Fabrication and Testing

Figure 7:
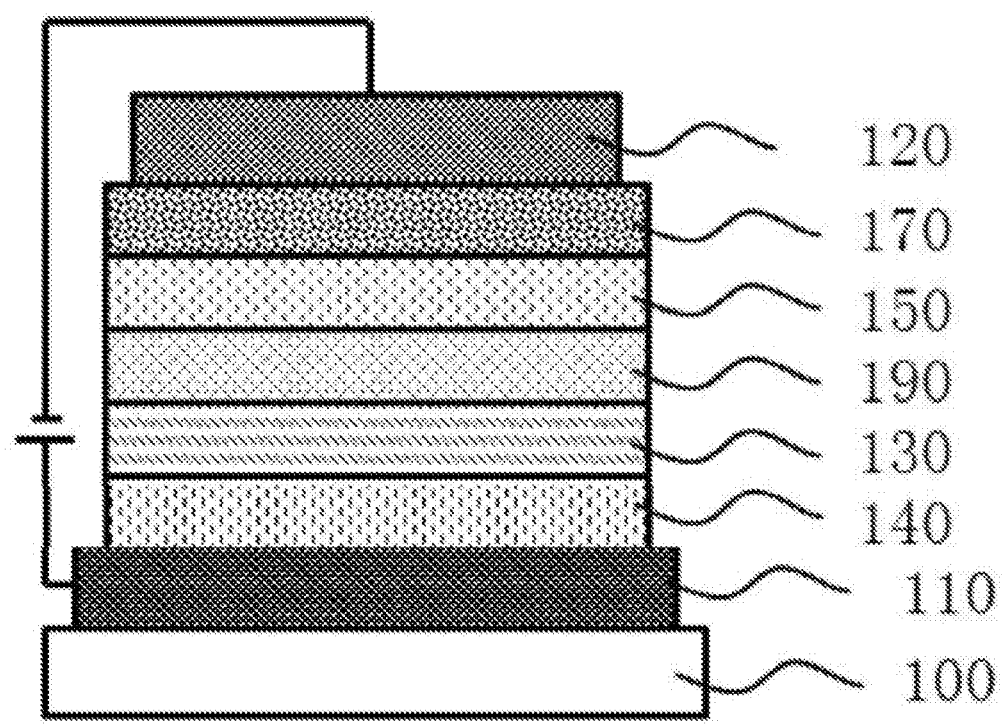
FIG. 7 illustrates a schematic diagram of another exemplary OLED consistent with disclosed embodiments.

To evaluate the performance of the disclosed organic optoelectronic devices, six exemplary organic optoelectronic devices (named as $1^{st}$ disclosed organic optoelectronic device to the $5^{th}$ disclosed organic optoelectronic device), and two reference organic optoelectronic devices (named as $1^{st}$ reference organic optoelectronic device and the $2^{nd}$ reference organic optoelectronic device) were fabricated. The $1^{st}$ to the $5^{th}$ disclosed organic optoelectronic devices and the $1^{st}$ to the $2^{nd}$ reference organic optoelectronic devices have the same structure shown in FIG. 7, except that the materials for forming various layers are different.

To fabricate the $1^{st}$ disclosed organic optoelectronic device, a substrate coated with a 100-nm-thick ITO film as the anode 110 was ultrasonically cleaned with distilled water, acetone, isopropanol, then dried in an oven, treated with for 30 minutes, and transferred to a vacuum evaporation chamber. Various organic films were vapor-deposited under a vacuum of 2×10-6 Pa. 60-nm-thick diphenylnaphthalenediamine (NPD) film and 10-thick 4,4', 4"-tris (N-carbazolyl) triphenylamine (TCTA) film were vapor-deposited on the anode 110 to form a hole transport layer (HTL) 140. 6 wt % Ir (ppy)$_3$ was used as the green phosphorescent dopant material and 94 wt % Compound 1 was used as the host material, which were vapor-deposited on the bole transport layer (WM) 140 to form a 30-nm-thick light-emitting layer 130.

Then, bis (8-hydroxy-2-methylquinoline)-diphenol aluminum (BAlq) was vapor-deposited on the light-emitting layer 130 to form a 5-nm-thick hole blocking layer (HBL) 190. 4,7-diphenyl-1,10-phenanthroline (Bphen) was vapor-deposited on the hole blocking layer (HBL) 190 to form a 20-nm-thick electron transport layer (ETL) 150. 1-nm-thick LiF and 100-nm-thick Al were successively deposited as an electron injection layer (EIL) 170 and the cathode 120 on the electron transport layer (ETL) 150, respectively. The fabricated $1^{st}$ disclosed organic optoelectronic device has a structure of ITO (100 nm)/NPD (60 nm)/TCTA (10 nm)/Ir (ppy)$_3$: Compound 1 (6 wt %; 94 wt. %, 30 nm)/BAlq (5 nm)/Bphen (20 nm)/LiF (1 nm)/Al (100 nm). (100 nm).

The $2^{nd}$ disclosed organic optoelectronic device was fabricated in the same manner as $1^{st}$ disclosed organic optoelectronic device, except that Compound 63 was adopted instead of Compound 1 as the host material in the $2^{nd}$ disclosed organic optoelectronic device.

The $3^{rd}$ disclosed organic optoelectronic device was fabricated in the same manner as $1^{st}$ disclosed organic opt electronic device, except that Compound 64 was adopted instead of Compound 1 as the host material in the $3^{rd}$ disclosed organic optoelectronic device.

The $1^{st}$ reference organic optoelectronic device was fabricated in the same manner as $1^{st}$ disclosed organic optoelectronic device, except that 6 wt % Ir (ppy)$_3$ was adopted as the dopant material, and 94 wt % CBP was adopted as the host material, which were vapor-deposited on the hole transport layer (HTL) 140 to form a 30-nm-thick light-emitting layer 130.

The $4^{th}$ disclosed organic optoelectronic device was fabricated in the same manner as $1^{st}$ disclosed organic optoelectronic device, except that 5 wt % Compound 2 was adopted as the dopant material, and 95 wt % DPEPO was adopted as the host material, which were vapor-deposited on the hole transport layer (HIT) 140 to form a 30-nm-thick light-emitting layer 130.

The fabricated $4^{th}$ disclosed organic optoelectronic device has a structure of ITO (100 nm)/NPD (60 nm)/TCTA (10 nm)/Compound 2: DPEPO (5 wt %: 95 wt %, 30 nm)/BAlq (5 nm)/Bphen (20 nm) LiF (1 nm)/Al (100 nm).

The $5^{th}$ disclosed organic optoelectronic device was fabricated in the same manner as $4^{th}$ disclosed organic optoelectronic device, except that Compound 43 was adopted instead of Compound 2 as the dopant material in the $5^{th}$ disclosed organic optoelectronic device.

The $2^{nd}$ reference organic optoelectronic device was fabricated in the same manner as $4^{th}$ disclosed organic optoelectronic device, except that 5 wt % DPAVB was adopted as the dopant material, and 95 wt % DPEPO was adopted as the host material, which were vapor-deposited on the hole transport layer (HTL) 140 to form a 30-nm-thick light-emitting layer 130.

The chemical formulas of DPAVB, DPEPO, Ir(ppy)$_3$, BAlq, Bphen, a-NPD, TCTA, and CBP are shown below.

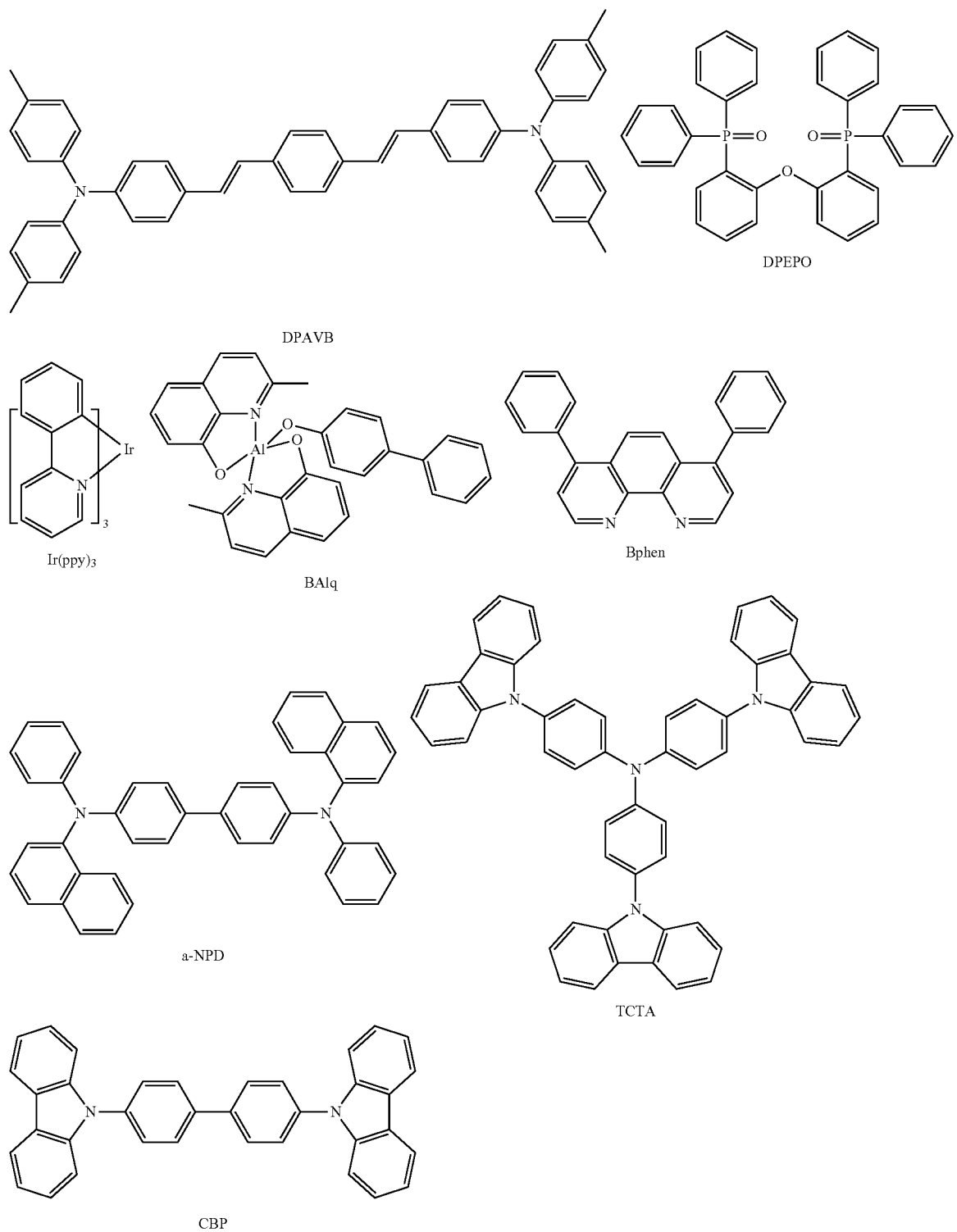

The current of the 1st to 5th disclosed organic optoelectronic devices and the 1st to 2nd reference organic optoelectronic devices under different voltages was measure by Keithley 2365A digital nanovolt meter, respectively. Then the corresponding current density was calculated by dividing the current by the light-emitting area. The luminance and radiant energy density of the 1st to 5th disclosed organic optoelectronic devices and the 1st to 2nd reference organic optoelectronic devices under different voltages was measure by Konicaminolta CS-2000 spectrophotometer, respectively. Based on the current density and the luminance under different voltages, the current efficiency (Cd/A) and the external quantum efficiency (EQE) under a given current density (0.1 mA/cm$^2$) was obtained.

The testing results of the 1st to 3rd disclosed organic optoelectronic devices in which the disclosed compounds are used as the host material and the 1st reference organic optoelectronic device are shown in the following Table 2.

TABLE 2

Testing results of the 1st to 3rd disclosed organic optoelectronic devices and the 1st reference organic optoelectronic device

| | Voltage(V) | Current efficiency (Cd/A) | EQE (%) | Color |
|---|---|---|---|---|
| 1st disclosed organic optoelectronic device | 4.7 | 43.3 | 17.1 | Green |
| 2nd disclosed organic optoelectronic device | 4.8 | 44.3 | 17.3 | Green |
| 3rd disclosed organic optoelectronic device | 4.7 | 41.8 | 16.6 | Green |
| 1st reference organic optoelectronic device | 5.1 | 40.3 | 15.6 | Green |

The testing results of the 4th to 5th disclosed organic optoelectronic devices in which the disclosed compounds are used as the guest dopant material and the 2nd reference organic optoelectronic device are shown in the following Table 3.

TABLE 3

Testing results of the 4th to 5th disclosed organic optoelectronic devices and the 2nd reference organic optoelectronic device

| | Voltage(V) | Current efficiency (Cd/A) | EQE (%) | Color |
|---|---|---|---|---|
| 4th disclosed organic optoelectronic device | 6.9 | 9.0 | 7.6 | Blue |
| 5th disclosed organic optoelectronic device | 7.6 | 8.2 | 6.9 | Blue |
| 2nd reference organic optoelectronic device | 8.8 | 5.5 | 4.9 | Blue |

According to the testing results shown Table 2, under the same current density (0.1 mA/cm²), the 1st to 3rd disclosed organic optoelectronic devices have a driving voltage lower than 5V, current efficiency higher than 39 Cd/A, and external quantum efficiency (EQE) largher than 15. That is, the disclosed compounds may enable the 1st to 4th disclosed organic optoelectronic devices to have a lower driving voltage, higher current efficiency and external quantum efficiency (EQE). The testing results shown in Table 2 may indicate that the disclosed compounds may be used as host materials.

According to the testing results shown ire Table 3, under the same current density (0.1 mA/cm²), the 4th to 5th disclosed organic optoelectronic devices have a lower driving voltage, higher current efficiency and external quantum efficiency (EQE) than the 2nd reference organic optoelectronic device. The testing results shown in Table 3 may indicate that the disclosed compounds may be used as dopant materials or co-doping materials. According to the testing results shown in Table 2 and Table 3, the optoelectronic device comprising the disclosed compounds may have excellent luminescent properties.

The other disclosed compounds may also enable the corresponding organic optoelectronic devices to have a lower driving voltage, higher current efficiency and external quantum efficiency (EQE), i.e., excellent luminescent properties.

The description of the disclosed embodiments is provided to illustrate the present disclosure to those skilled in the art. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. A compound of the following chemical formula (I):

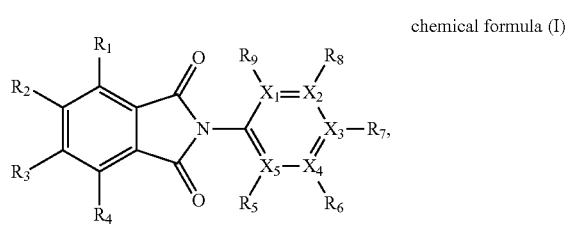

chemical formula (I)

wherein:
in the chemical formula (I), $X_1$ to $X_5$ are independently selected from the group consisting of C and N, and at least one of $X_1$ to $X_5$ are selected from N, and when N is selected, a substituent is not included;

$R_1$ to $R_9$ are independently selected from the group consisting of hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II):

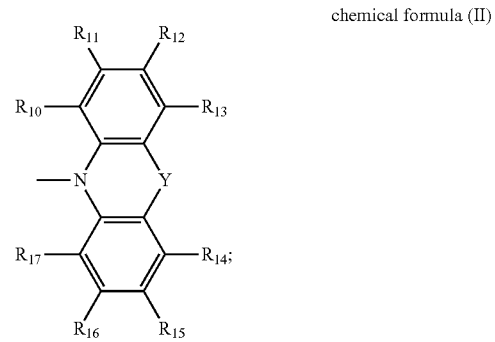

chemical formula (II)

and
at least one of $R_5$ to $R_9$ is selected from the chemical group A,
wherein in the chemical formula (II),
$R_{10}$ to $R_{17}$ are independently selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl; and
Y is selected from the group consisting of O, S, substituted or unsubstituted imino, substituted or unsubstituted methylene, and substituted or unsubstituted silylene, and a substituent is selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl.

2. The compound according to claim 1 has the following chemical formula (IV):

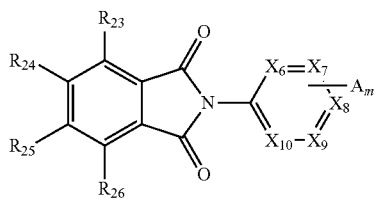

the chemical formula (IV),
- wherein $X_6$ to $X_{10}$ are independently selected from the group consisting of C and N, and at least three of $X_6$ to $X_{10}$ are selected from C;
- when N is selected, a substituent is not included;
- $R_{23}$ to $R_{26}$ are independently selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl;
- the chemical group A is connected to a number m of C of $X_6$ to $X_{10}$, m is a positive integer, and $1 \leq m \leq 4$; and
- for a remaining C of $X_6$ to $X_{10}$, a substituent selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl is included.

3. The compound according to claim 1, wherein:
the heteroatom-substituted alkyl is selected from alkoxy groups.

4. The compound according to claim 1, wherein:
the $C_6$ to $C_{30}$ aryl is selected from the group consisting of phenyl and naphthyl.

5. The compound according to claim 1, wherein:
the $C_2$ to $C_{30}$ heteroaryl is selected from heteroaryl containing one or more N.

6. The compound according to claim 1, wherein:
the chemical group A is selected from the group consisting of:

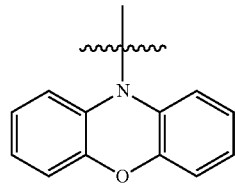 , 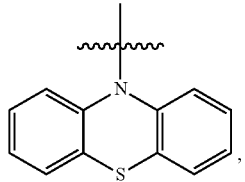 ,

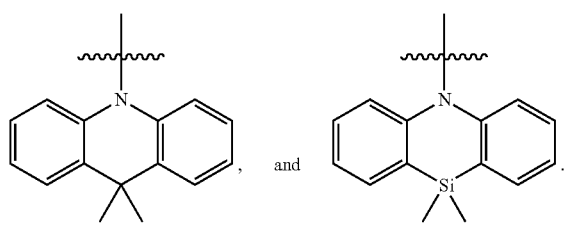 and 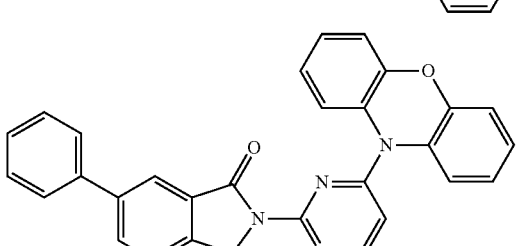 .

7. The compound according to claim 1, comprising a compound selected from the group consisting of:

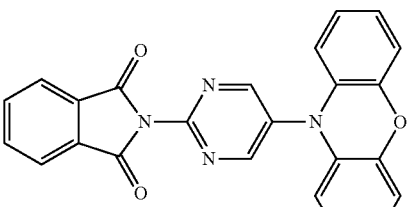

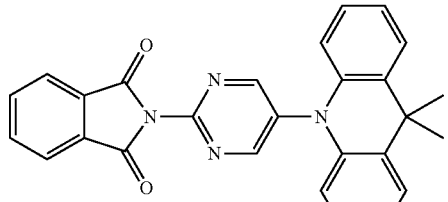

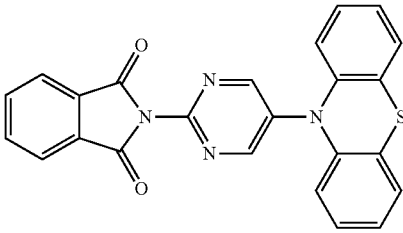

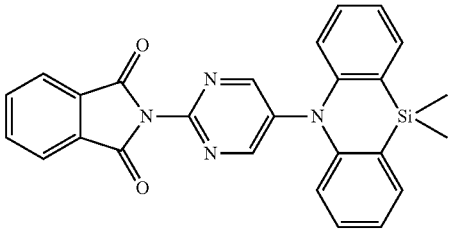

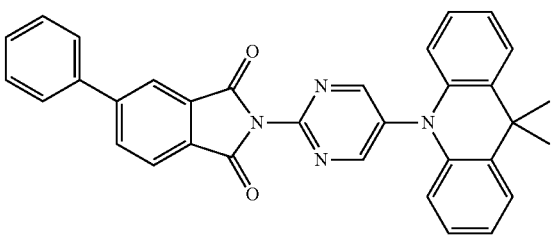

47
-continued

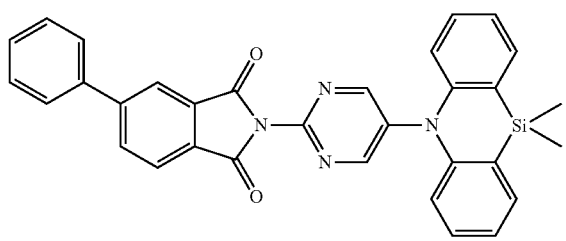
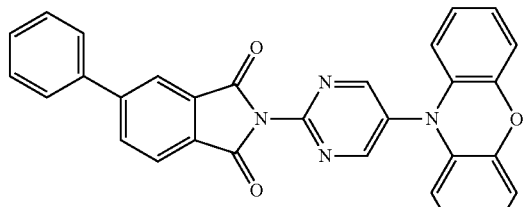
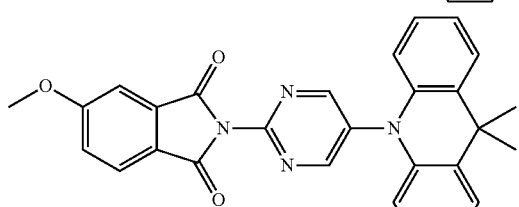
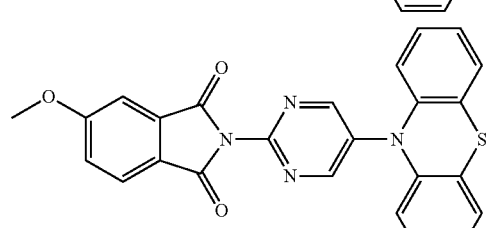
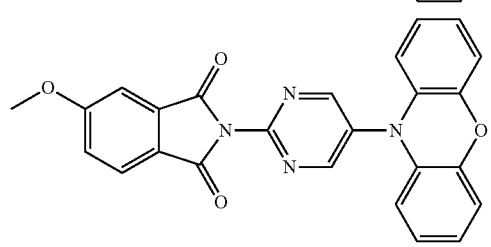
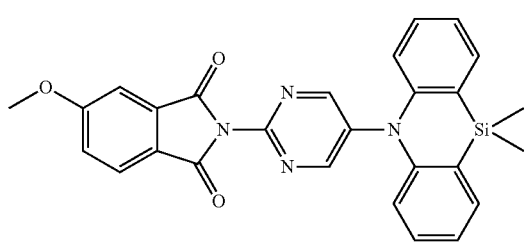
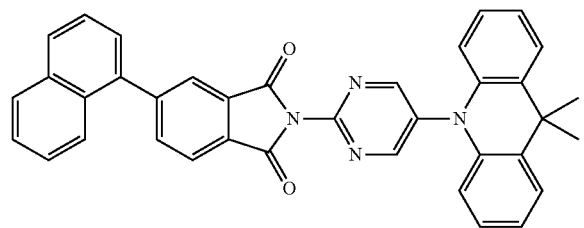

48
-continued

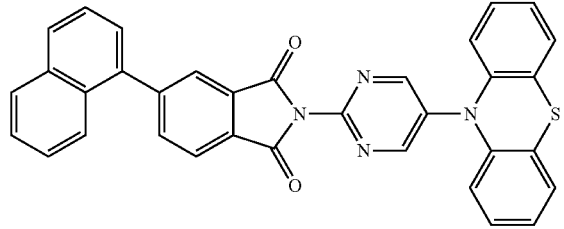
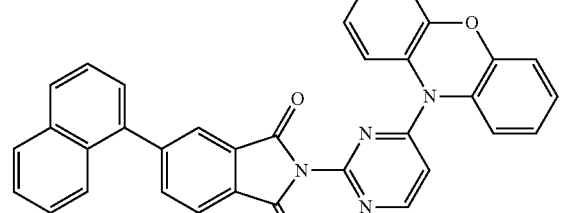
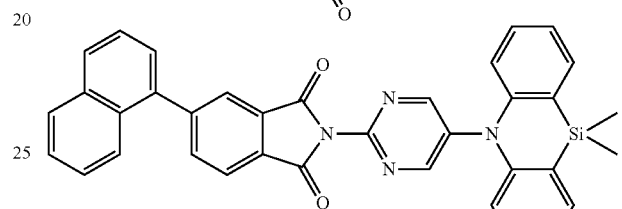
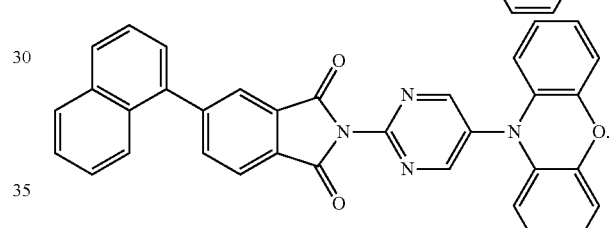

8. The compound according to claim 1, wherein:
an energy difference between a lowest singlet excited state $S_1$ and a lowest triplet excited state $T_1$ of the compound is configured to be $\Delta E_{st} \leq 0.30$ eV.

9. The compound according to claim 8, wherein:
the energy difference between the lowest singlet excited state $S_1$ and the lowest triplet excited state $T_1$ of the compound is configured to be $\Delta E_{st} \leq 0.02$ eV.

10. An organic optoelectronic device, comprising:
an anode;
a cathode; and
one or more organic thin film layers disposed between the anode and the cathode,
wherein at least one of the one or more organic thin film layers includes one or more compounds each having the following chemical formula (I):

chemical formula (I)

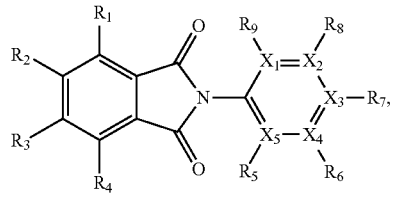

wherein:
in the chemical formula (I), $X_1$ to $X_5$ are independently selected from the group consisting of C and N, and at least one of $X_1$ to $X_5$ are selected from N, and when N is selected, a substituent is not included;
$R_1$ to $R_9$ are independently selected from the group consisting of hydrogen, deuterium, $C_1$ to $C_{30}$ alkyl, $C_1$ to $C_{30}$ heteroatom-substituted alkyl, $C_6$ to $C_{30}$ aryl, $C_2$ to $C_{30}$ heteroaryl, and a chemical group A represented by the following chemical formula (II):

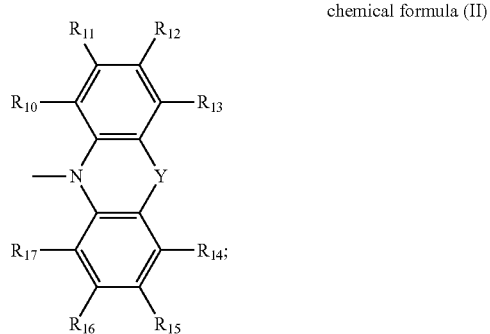

chemical formula (II)

and
at least one of $R_5$ to $R_9$ is selected from the chemical group A, wherein in the chemical formula (II),
$R_{10}$ to $R_{17}$ are independently selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl; and
Y is selected from the group consisting of O, S, substituted or unsubstituted imino, substituted or unsubstituted methylene, and substituted or unsubstituted silylene, and a substituent is selected from the group consisting of hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl.

11. The organic optoelectronic device according to claim 10, wherein:
the one or more compounds are heat activated delayed fluorescence (TADF) materials.

12. The organic optoelectronic device according to claim 10, wherein:
the at least one of the one or more organic thin film layers disposed between the anode and the cathode is a light-emitting layer, wherein the light-emitting layer includes the one or more compounds.

13. The organic optoelectronic device according to claim 12, wherein:
the one or more compounds are used as a dopant material, a co-doping material, or a host material in the light-emitting layer.

14. The organic optoelectronic device according to claim 10, wherein:
the one or more organic thin film layers further include at least one layer selected from the group consisting of a hole transport layer, a hole injection layer, an electron blocking layer, a hole blocking layer, an electron transport layer, and an electron injection layer.

15. The organic optoelectronic device according to claim 14, wherein:
the at least one layer selected from the group of the hole transport layer, the hole injection layer, the electron blocking layer, the hole blocking layer, the electron transport layer, and the electron injection layer includes the one or more compounds.

16. The organic optoelectronic device according to claim 14, wherein:
the one or more organic thin film layers further include the hole transport layer disposed between the light-emitting layer and the anode.

17. The organic optoelectronic device according to claim 14, wherein:
the one or more organic thin film layers further include the hole transport layer and the electron transport layer,
wherein the hole transport layer is disposed between the light-emitting layer and the anode, and
the electron transport layer is disposed between the light-emitting layer and the cathode.

18. The organic optoelectronic device according to claim 14, wherein:
the one or more organic thin film layers further include the hole transport layer, the electron transport layer, the electron injection layer and the hole injection layer,
wherein the hole transport layer and the hole injection layer are disposed between the light-emitting layer and the anode, and
the electron transport layer and the electron injection layer are disposed between the light-emitting layer and the cathode.

19. The organic optoelectronic device according to claim 14, wherein:
the one or more organic thin film layers further include the hole transport layer, the electron transport layer, the electron injection layer, the hole injection layer, the electron blocking layer, and the hole blocking layer,
wherein the electron blocking layer, the hole transport layer and the hole injection layer are disposed between the light-emitting layer and the anode, and
the hole blocking layer, the electron transport layer and the electron injection layer are disposed between the light-emitting layer and the cathode.

* * * * *